(12) United States Patent
Modzelewski et al.

(10) Patent No.: US 6,541,266 B2
(45) Date of Patent: Apr. 1, 2003

(54) METHOD FOR DETERMINING CONCENTRATION OF AN ANALYTE IN A TEST STRIP

(75) Inventors: Brent E. Modzelewski, Brookfield, CT (US); Steven B. Gilmour, Coral Gables, FL (US); G. Thomas Roth, Fairfield, CT (US); Douglas E. Bell, Coral Springs, FL (US)

(73) Assignee: Home Diagnostics, Inc., Ft. Lauderdale, FL (US)

( * ) Notice: Subject to any disclaimer, the term of this patent is extended or adjusted under 35 U.S.C. 154(b) by 206 days.

(21) Appl. No.: 09/794,045

(22) Filed: Feb. 28, 2001

(65) Prior Publication Data

US 2002/0146835 A1 Oct. 10, 2002

(51) Int. Cl.$^7$ .......................... G01N 33/00; G01N 21/00
(52) U.S. Cl. .......................... 436/95; 436/164; 436/169; 422/55; 422/56; 422/82.05; 422/82.09; 435/14
(58) Field of Search .......................... 436/14, 95, 164, 436/165, 169, 170; 422/55, 56, 61, 82.05, 82.09; 435/14

(56) References Cited

U.S. PATENT DOCUMENTS

| | | |
|---|---|---|
| 2,297,248 A | 9/1942 | Rudolph |
| 2,369,499 A | 2/1945 | Treuhaft |
| 2,893,843 A | 7/1959 | Adams |
| 2,893,844 A | 7/1959 | Cook |
| 3,061,523 A | 10/1962 | Free |
| 3,092,465 A | 6/1963 | Adams |
| 3,099,605 A | 7/1963 | Free |
| 3,127,281 A | 3/1964 | Meyer |
| 3,232,710 A | 2/1966 | Rieckmann |
| 3,298,789 A | 1/1967 | Mast |
| 3,413,198 A | 11/1968 | Deutsch |

(List continued on next page.)

FOREIGN PATENT DOCUMENTS

| | | |
|---|---|---|
| AU | 45033/85 | 1/1986 |
| AU | 76758/87 | 2/1988 |
| CA | 1117784 | 2/1982 |
| CA | 1219797 | 3/1987 |
| DE | 34 39 181 | 10/1984 |
| DE | 39 21 391 | 1/1991 |
| EP | 0 095 057 | 11/1983 |

(List continued on next page.)

OTHER PUBLICATIONS

Adler, S. et al., "Automatic Coagulation Profile System," Advances in Automated Analysis, Technicon International Congress 1970, vol. 1, pp. 421–424 (1971).

(List continued on next page.)

*Primary Examiner*—Maureen M. Wallenhorst
(74) *Attorney, Agent, or Firm*—Finnegan, Henderson, Farabow, Garrett & Dunner LLP

(57) ABSTRACT

The present invention provides a method of measuring an analyte, such as glucose in a fluid sample, such as whole blood, by a reflectance reading device. The method includes making periodic intermediate calculations of analyte level and dynamically ascertaining when an analytical reaction has reached an end point. Once stable, the process stops making periodic calculations and reports the final, actual glucose concentration. According to an exemplary embodiment, the method is performed by a reflectance photometer using an analytical test strip containing reagents that react with an analyte of interest in the test fluid. The end point is determined by calculating an intermediate analyte level of the testing element at predetermined intervals and calculating a ratio value corresponding to the $(n)^{th}$ measurement to an $(n-5)^{th}$ measurement. When two consecutive ratio values are less than or equal to a predetermined value, the end point is deemed reached and the final analyte level ascertained.

36 Claims, 5 Drawing Sheets

U.S. PATENT DOCUMENTS

| | | |
|---|---|---|
| 3,443,903 A | 5/1969 | Haack |
| 3,483,031 A | 12/1969 | Lauer |
| 3,501,009 A | 3/1970 | Jaworek |
| 3,506,126 A | 4/1970 | Serfass |
| 3,509,025 A | 4/1970 | Bergmeyer |
| 3,511,608 A | 5/1970 | Anderson |
| 3,552,925 A | 1/1971 | Fetter |
| 3,552,928 A | 1/1971 | Fetter |
| 3,560,161 A | 2/1971 | Webb |
| 3,577,162 A | 5/1971 | Gaehwiler |
| 3,591,480 A | 7/1971 | Neff |
| 3,593,568 A | 7/1971 | Schmitz |
| 3,604,815 A | 9/1971 | Clemens |
| 3,607,093 A | 9/1971 | Stone |
| 3,620,677 A | 11/1971 | Morison |
| 3,630,957 A | 12/1971 | Rey |
| 3,650,698 A | 3/1972 | Adler |
| 3,653,836 A | 4/1972 | Gruber |
| 3,658,480 A | 4/1972 | Kane |
| 3,660,638 A | 5/1972 | Oberli |
| 3,663,175 A | 5/1972 | Depositar |
| 3,672,838 A | 6/1972 | Trcka |
| 3,677,901 A | 7/1972 | Bergmeyer |
| 3,690,833 A | 9/1972 | Ferrari |
| 3,703,336 A | 11/1972 | Rosse |
| 3,709,612 A | 1/1973 | Clemens |
| 3,713,986 A | 1/1973 | Bergmeyer |
| 3,715,192 A | 2/1973 | Wenz |
| 3,718,439 A | 2/1973 | Rosse |
| 3,723,064 A | 3/1973 | Liotta |
| 3,748,044 A | 7/1973 | Liston |
| 3,762,609 A | 10/1973 | Hagen |
| 3,765,841 A | 10/1973 | Paulson |
| 3,769,178 A | 10/1973 | Rothermel |
| 3,775,058 A | 11/1973 | Bush |
| 3,775,595 A | 11/1973 | Rosse |
| 3,778,350 A | 12/1973 | Bergmeyer |
| 3,785,772 A | 1/1974 | Coggeshall |
| 3,791,933 A | 2/1974 | Moyer |
| 3,795,149 A | 3/1974 | Gillette |
| 3,795,484 A | 3/1974 | Daly |
| 3,798,004 A | 3/1974 | Zerachia |
| 3,802,843 A | 4/1974 | Kim |
| 3,804,593 A | 4/1974 | Smythe |
| 3,811,840 A | 5/1974 | Bauer |
| 3,814,582 A | 6/1974 | Rohrbaugh |
| 3,819,863 A | 6/1974 | Slaght |
| 3,822,285 A | 7/1974 | Werner |
| 3,837,339 A | 9/1974 | Aisenberg et al. |
| 3,847,553 A | 11/1974 | Verbeck |
| 3,853,472 A | 12/1974 | Rittersdorf |
| 3,864,166 A | 2/1975 | Barker |
| 3,876,374 A | 4/1975 | Burns |
| 3,881,992 A | 5/1975 | Ralston |
| 3,897,214 A | 7/1975 | Lange |
| 3,901,657 A | 8/1975 | Lightfoot |
| 3,902,052 A | 8/1975 | Amar |
| 3,907,503 A | 9/1975 | Betts |
| 3,910,701 A | 10/1975 | Henderson |
| 3,915,647 A | 10/1975 | Wright |
| 3,917,452 A | 11/1975 | Rittersdorf |
| 3,917,453 A | 11/1975 | Milligan |
| 3,919,051 A | 11/1975 | Koch |
| 3,926,736 A | 12/1975 | Bucolo |
| 3,929,581 A | 12/1975 | de Fonseca-Wollheim |
| 3,933,593 A | 1/1976 | Sternberg |
| 3,936,357 A | 2/1976 | Milligan |
| 3,942,995 A | 3/1976 | Ichikawa |
| 3,950,133 A | 4/1976 | Monte |
| 3,954,342 A | 5/1976 | Boeke |
| 3,957,436 A | 5/1976 | Murray |
| 3,958,560 A | 5/1976 | March |
| 3,960,497 A | 6/1976 | Acord |
| 3,964,870 A | 6/1976 | Tiedemann |
| 3,971,630 A | 7/1976 | Sandrock |
| 3,973,129 A | 8/1976 | Blumberg |
| 3,973,189 A | 8/1976 | Angel |
| 3,975,398 A | 8/1976 | Werner |
| 3,979,274 A | 9/1976 | Newman |
| 3,980,437 A | 9/1976 | Kishimoto |
| 3,983,005 A | 9/1976 | Goodhue |
| 3,985,508 A | 10/1976 | Williams |
| 3,986,833 A | 10/1976 | Mast |
| 3,988,208 A | 10/1976 | Werner |
| 3,990,849 A | 11/1976 | Lee |
| 3,992,158 A | 11/1976 | Przybylowicz |
| 4,009,615 A | 3/1977 | Ruhl |
| 4,011,046 A | 3/1977 | Labes |
| 4,014,321 A | 3/1977 | March |
| 4,015,121 A | 3/1977 | Gagnon |
| 4,022,577 A | 5/1977 | Brooker |
| 4,038,485 A | 7/1977 | Johnston |
| 4,040,786 A | 8/1977 | Trivedi |
| 4,042,335 A | 8/1977 | Clement |
| 4,043,756 A | 8/1977 | Sommervold |
| 4,050,898 A | 9/1977 | Goffe |
| 4,056,468 A | 11/1977 | Breiter |
| 4,057,394 A | 11/1977 | Genshaw |
| 4,059,405 A | 11/1977 | Sodickson |
| 4,061,468 A | 12/1977 | Lange |
| 4,061,469 A | 12/1977 | DuBose |
| 4,066,362 A | 1/1978 | Carter |
| 4,066,403 A | 1/1978 | Bruschi |
| 4,068,169 A | 1/1978 | Angel |
| 4,069,017 A | 1/1978 | Wu |
| 4,076,502 A | 2/1978 | Dugle |
| 4,095,272 A | 6/1978 | Janzen |
| 4,098,574 A | 7/1978 | Dappen |
| 4,101,276 A | 7/1978 | Anderson |
| 4,109,159 A | 8/1978 | Onillon |
| 4,110,079 A | 8/1978 | Schaeffer |
| 4,125,327 A | 11/1978 | Margolis |
| 4,125,372 A | 11/1978 | Kawai |
| 4,128,628 A | 12/1978 | Brooker |
| 4,135,883 A | 1/1979 | McNeil |
| 4,144,306 A | 3/1979 | Figueras |
| 4,152,390 A | 5/1979 | Nosco |
| 4,153,668 A | 5/1979 | Hill |
| 4,160,646 A | 7/1979 | Furutani |
| 4,165,508 A | 8/1979 | Barter |
| 4,176,008 A | 11/1979 | Figueras |
| 4,178,153 A | 12/1979 | Sodickson |
| 4,180,060 A | 12/1979 | Kutter |
| 4,199,260 A | 4/1980 | Kusnetz |
| 4,199,261 A | 4/1980 | Tidd |
| 4,211,845 A | 7/1980 | Genshaw |
| 4,217,107 A | 8/1980 | Saito |
| 4,218,144 A | 8/1980 | Whitehouse et al. |
| 4,219,529 A | 8/1980 | Tersteeg |
| 4,224,032 A | 9/1980 | Glover |
| 4,226,537 A | 10/1980 | Colley |
| 4,230,456 A | 10/1980 | Wu |
| 4,233,029 A | 11/1980 | Columbus |
| 4,238,196 A | 12/1980 | Acuff |
| 4,240,912 A | 12/1980 | Stumpf |
| 4,253,846 A | 3/1981 | Smythe |
| 4,254,083 A | 3/1981 | Columbus |
| 4,255,384 A | 3/1981 | Kitajima |
| 4,255,788 A | 3/1981 | Schwartz |
| 4,256,693 A | 3/1981 | Kondo |
| 4,257,862 A | 3/1981 | Schnipelsky |

| Patent | Date | Name |
|---|---|---|
| 4,258,001 A | 3/1981 | Pierce |
| 4,261,041 A | 4/1981 | Starr |
| 4,269,938 A | 5/1981 | Frank |
| 4,272,482 A | 6/1981 | Jessop |
| 4,273,868 A | 6/1981 | Walter |
| 4,274,832 A | 6/1981 | Wu |
| 4,276,051 A | 6/1981 | Ginsberg |
| 4,277,561 A | 7/1981 | Monget |
| 4,278,439 A | 7/1981 | White |
| 4,281,062 A | 7/1981 | Kallis |
| 4,283,383 A | 8/1981 | Masson |
| 4,283,491 A | 8/1981 | Dappen |
| 4,288,228 A | 9/1981 | Oberhardt |
| 4,292,272 A | 9/1981 | Kitajima |
| 4,297,238 A | 10/1981 | Vormbrock |
| 4,298,345 A | 11/1981 | Sodickson |
| 4,298,688 A | 11/1981 | Kallies |
| 4,299,916 A | 11/1981 | Litman |
| 4,300,906 A | 11/1981 | Negersmith |
| 4,302,420 A | 11/1981 | Jakubowicz |
| 4,303,406 A | 12/1981 | Ross |
| 4,303,408 A | 12/1981 | Kim |
| 4,303,753 A | 12/1981 | Lam |
| 4,308,485 A | 12/1981 | Ignazio |
| 4,310,399 A | 1/1982 | Columbus |
| 4,312,834 A | 1/1982 | Vogel |
| 4,318,984 A | 3/1982 | Magers |
| 4,318,985 A | 3/1982 | Bauer |
| 4,325,910 A | 4/1982 | Jordan |
| 4,330,299 A | 5/1982 | Cerami |
| 4,336,330 A | 6/1982 | Bauer |
| 4,337,065 A | 6/1982 | Hiratsuka |
| 4,338,279 A | 7/1982 | Orimo |
| 4,340,669 A | 7/1982 | Bauer |
| 4,353,983 A | 10/1982 | Siddiqi |
| 4,353,984 A | 10/1982 | Yamada |
| 4,361,648 A | 11/1982 | Shuenn-tzong |
| 4,363,874 A | 12/1982 | Greenquist |
| 4,366,061 A | 12/1982 | Papanek et al. |
| 4,366,241 A | 12/1982 | Tom |
| 4,370,983 A | 2/1983 | Lichtenstein |
| 4,373,818 A | 2/1983 | Yamamoto |
| 4,384,042 A | 5/1983 | Milke |
| 4,390,343 A | 6/1983 | Walter |
| 4,390,621 A | 6/1983 | Bauer |
| 4,391,905 A | 7/1983 | Bauer |
| 4,391,906 A | 7/1983 | Bauer |
| 4,399,099 A | 8/1983 | Buckles |
| 4,403,984 A | 9/1983 | Ash |
| 4,407,959 A | 10/1983 | Tsuji |
| 4,415,700 A | 11/1983 | Betz |
| 4,418,037 A | 11/1983 | Katsuyama |
| 4,420,564 A | 12/1983 | Tsuji |
| 4,420,566 A | 12/1983 | Jessop |
| 4,427,632 A | 1/1984 | Okaniwa |
| 4,427,889 A | 1/1984 | Muller |
| 4,430,299 A | 2/1984 | Horne |
| 4,430,427 A | 2/1984 | Hopkins |
| 4,430,436 A | 2/1984 | Koyama |
| 4,448,207 A | 5/1984 | Parrish |
| 4,449,538 A | 5/1984 | Corbitt et al. ............... 128/70 |
| 4,450,153 A | 5/1984 | Hopkins |
| 4,452,887 A | 6/1984 | Kitajima |
| 4,458,539 A | 7/1984 | Bilstad |
| 4,459,358 A | 7/1984 | Berke |
| 4,460,684 A | 7/1984 | Bauer |
| 4,464,172 A | 8/1984 | Lichtenstein |
| 4,472,498 A | 9/1984 | Masuda |
| 4,472,505 A | 9/1984 | Manabe |
| 4,476,222 A | 10/1984 | Ohtani |
| 4,477,575 A | 10/1984 | Vogel |
| 4,478,942 A | 10/1984 | Katsuyama |
| 4,478,944 A | 10/1984 | Gross |
| 4,483,924 A | 11/1984 | Tsuji |
| 4,492,462 A | 1/1985 | Pross |
| 4,499,052 A | 2/1985 | Fulwyler |
| 4,503,385 A | 3/1985 | Haynes |
| 4,503,555 A | 3/1985 | Brimhall, Jr. |
| 4,509,859 A | 4/1985 | Markart |
| 4,517,160 A | 5/1985 | Galle |
| 4,518,259 A | 5/1985 | Ward |
| 4,523,853 A | 6/1985 | Rosenbaldt et al. |
| 4,528,159 A | 7/1985 | Liston |
| 4,532,107 A | 7/1985 | Siddigi |
| 4,534,012 A | 8/1985 | Yokozawa |
| 4,540,670 A | 9/1985 | Arai |
| 4,547,460 A | 10/1985 | Eikenberry |
| 4,551,307 A | 11/1985 | Koyama |
| 4,552,458 A | 11/1985 | Lowne |
| 4,553,848 A | 11/1985 | Rosicke |
| 4,554,132 A | 11/1985 | Collins |
| 4,557,901 A | 12/1985 | Koyama |
| 4,562,148 A | 12/1985 | Sommer |
| 4,567,024 A | 1/1986 | Koyama |
| 4,576,793 A | 3/1986 | Koyama |
| 4,578,245 A | 3/1986 | Arai |
| 4,578,248 A | 3/1986 | Nagaoka |
| 4,587,100 A | 5/1986 | Amano |
| 4,587,220 A | 5/1986 | Mayambala-Mwanika |
| 4,592,365 A | 6/1986 | Georgi |
| 4,592,893 A | 6/1986 | Poppe |
| 4,594,224 A | 6/1986 | Okaniwa |
| 4,594,327 A | 6/1986 | Zuk |
| 4,595,562 A | 6/1986 | Liston |
| 4,602,995 A | 7/1986 | Cassaday |
| 4,603,428 A | 7/1986 | Sandrik |
| 4,604,254 A | 8/1986 | Yamamoto |
| 4,604,264 A | 8/1986 | Rothe |
| 4,604,579 A | 8/1986 | Cannon |
| 4,618,475 A | 10/1986 | Wang |
| 4,622,207 A | 11/1986 | Wang |
| 4,627,014 A | 12/1986 | Lo |
| 4,627,445 A | 12/1986 | Garcia |
| 4,632,559 A | 12/1986 | Brunsting |
| 4,637,403 A | 1/1987 | Garcia |
| 4,637,978 A | 1/1987 | Dappen |
| 4,642,286 A | 2/1987 | Moldowan |
| 4,647,430 A | 3/1987 | Zweig |
| 4,647,432 A | 3/1987 | Wakatake |
| 4,649,123 A | 3/1987 | Charlton |
| 4,661,319 A | 4/1987 | Lape |
| 4,668,619 A | 5/1987 | Greenquist |
| 4,669,878 A | 6/1987 | Meier |
| 4,670,218 A | 6/1987 | Gantzer |
| 4,671,937 A | 6/1987 | Katsuyama |
| 4,676,653 A | 6/1987 | Strohmeier et al. |
| 4,685,059 A | 8/1987 | Yamamoto |
| 4,686,479 A | 8/1987 | Young |
| 4,687,329 A | 8/1987 | Schultz |
| 4,693,985 A | 9/1987 | Degen |
| 4,703,756 A | 11/1987 | Gough et al. |
| 4,710,458 A | 12/1987 | Maines |
| 4,714,341 A | 12/1987 | Hamaguri |
| 4,717,546 A | 1/1988 | Barnett |
| 4,731,726 A | 3/1988 | Allen |
| 4,732,736 A | 3/1988 | Kobayashi |
| 4,734,360 A | 3/1988 | Phillips |
| 4,748,114 A | 5/1988 | Kallies |
| 4,772,561 A | 9/1988 | Genshaw |
| 4,773,097 A | 9/1988 | Suzaki |
| 4,774,192 A | 9/1988 | Terminiello |
| 4,775,637 A | 10/1988 | Sutherland |

| Patent | Date | Inventor | Class |
|---|---|---|---|
| 4,780,283 A | 10/1988 | Meinecke | |
| 4,782,511 A | 11/1988 | Nemec et al. | |
| 4,787,398 A | 11/1988 | Garcia | |
| 4,790,979 A | 12/1988 | Terminiello | |
| 4,791,461 A | 12/1988 | Kishimoto | |
| 4,803,153 A | 2/1989 | Shibata | |
| 4,803,159 A | 2/1989 | Smith-Lewis | |
| 4,803,625 A | 2/1989 | Fu | |
| 4,810,470 A | 3/1989 | Burkhardt | |
| 4,814,142 A | 3/1989 | Gleisner | |
| 4,816,224 A | 3/1989 | Vogel | |
| 4,818,710 A | 4/1989 | Sutherland | |
| 4,820,489 A | 4/1989 | Rothe | |
| 4,820,649 A | 4/1989 | Kawaguchi | |
| 4,824,639 A | 4/1989 | Hildenbrand | |
| 4,839,297 A | 6/1989 | Freitag | |
| 4,849,340 A | 7/1989 | Oberhardt | |
| 4,855,108 A | 8/1989 | Masuda | |
| 4,857,273 A | 8/1989 | Stewart | |
| 4,866,836 A | 9/1989 | Von Brandt et al. | |
| 4,870,005 A | 9/1989 | Akiyoshi | |
| 4,876,204 A | 10/1989 | Inoue | |
| 4,876,207 A | 10/1989 | Mack | |
| 4,877,747 A | 10/1989 | Stewart | |
| 4,889,131 A | 12/1989 | Salem et al. | |
| 4,889,815 A | 12/1989 | Bradwell | |
| 4,900,666 A | 2/1990 | Phillips | |
| 4,909,260 A | 3/1990 | Salem et al. | |
| 4,913,150 A | 4/1990 | Cheung et al. | 128/633 |
| 4,914,020 A | 4/1990 | Arai et al. | 435/4 |
| 4,929,561 A | 5/1990 | Hirschfeld | 436/116 |
| 4,931,384 A | 6/1990 | Layton et al. | 435/7 |
| 4,935,346 A * | 6/1990 | Phillips et al. | 422/56 |
| 4,937,050 A | 6/1990 | Meinecke et al. | 422/68.1 |
| 4,943,522 A | 7/1990 | Eisinger et al. | 435/7 |
| 4,949,400 A | 8/1990 | Leveen et al. | 356/400 |
| 4,950,454 A | 8/1990 | Masuda et al. | 422/56 |
| 4,952,515 A | 8/1990 | Gleisner | 436/169 |
| 4,962,021 A | 10/1990 | Meserol et al. | 435/7 |
| 4,965,047 A | 10/1990 | Hammond | 422/58 |
| 4,970,172 A | 11/1990 | Kundu | |
| 4,974,607 A | 12/1990 | Miwa | |
| 4,976,724 A | 12/1990 | Nieto et al. | 606/182 |
| 4,981,779 A | 1/1991 | Wagner | |
| 4,985,205 A | 1/1991 | Fritsche et al. | |
| 4,987,085 A | 1/1991 | Allen et al. | 436/169 |
| 4,994,238 A | 2/1991 | Daffern et al. | |
| 5,004,585 A | 4/1991 | Rayman | 422/58 |
| 5,019,574 A | 5/1991 | Miura et al. | |
| 5,023,052 A | 6/1991 | Nagatomo et al. | 422/56 |
| 5,023,053 A | 6/1991 | Finlan | 422/82.05 |
| 5,029,583 A | 7/1991 | Meserol et al. | |
| 5,035,863 A | 7/1991 | Finlan et al. | 422/82.05 |
| 5,036,852 A | 8/1991 | Leishman | |
| 5,039,225 A | 8/1991 | Uekusa | |
| 5,043,269 A | 8/1991 | Theodoropulos | 435/28 |
| 5,046,619 A | 9/1991 | Finlan | 422/82.05 |
| 5,047,206 A | 9/1991 | Dombrowski | 422/56 |
| 5,047,213 A | 9/1991 | Finlan et al. | 422/82.11 |
| 5,047,351 A | 9/1991 | Makiuchi et al. | 436/169 |
| 5,049,487 A | 9/1991 | Phillips et al. | |
| 5,055,265 A | 10/1991 | Finlan | 422/82.05 |
| 5,059,394 A | 10/1991 | Phillips et al. | |
| 5,067,093 A | 11/1991 | Przybylowicz et al. | 364/498 |
| 5,071,746 A | 12/1991 | Wilk et al. | 435/7.94 |
| 5,071,769 A | 12/1991 | Kundu | |
| 5,079,174 A | 1/1992 | Buck et al. | 436/538 |
| 5,079,715 A | 1/1992 | Venkataraman et al. | |
| 5,082,626 A | 1/1992 | Grage, Jr. | 422/56 |
| 5,096,809 A | 3/1992 | Chen et al. | 435/7.9 |
| 5,096,836 A | 3/1992 | Macho et al. | 436/169 |
| 5,104,619 A | 4/1992 | de Castro et al. | 422/56 |
| 5,104,793 A | 4/1992 | Buck | 435/7.92 |
| 5,104,811 A | 4/1992 | Berger et al. | 436/164 |
| 5,106,758 A | 4/1992 | Adler et al. | 436/165 |
| 5,110,550 A | 5/1992 | Schlipfenbacher et al. | 422/56 |
| 5,110,724 A | 5/1992 | Hewett | 435/11 |
| 5,114,350 A | 5/1992 | Hewett | |
| 5,114,673 A | 5/1992 | Berger et al. | 422/56 |
| 5,116,763 A | 5/1992 | Greene et al. | 436/95 |
| 5,120,507 A | 6/1992 | Sano et al. | 422/82.05 |
| 5,124,128 A | 6/1992 | Hildenbrand et al. | 422/56 |
| 5,128,171 A | 7/1992 | Gleisner | 427/2 |
| 5,130,231 A | 7/1992 | Kennedy et al. | 435/4 |
| 5,130,258 A | 7/1992 | Makino et al. | 436/169 |
| 5,147,606 A | 9/1992 | Charlton et al. | 422/56 |
| 5,149,505 A | 9/1992 | English et al. | 422/99 |
| 5,152,962 A | 10/1992 | Lackie | 422/681 |
| 5,166,051 A | 11/1992 | Killeen et al. | 435/7.1 |
| 5,171,688 A | 12/1992 | Hewett et al. | 435/289 |
| 5,173,261 A | 12/1992 | Krause et al. | 422/58 |
| 5,174,963 A | 12/1992 | Fuller et al. | 422/82.05 |
| 5,179,005 A | 1/1993 | Phillips et al. | |
| 5,179,288 A * | 1/1993 | Miffitt et al. | 250/564 |
| 5,183,741 A | 2/1993 | Arai et al. | 435/14 |
| 5,187,100 A | 2/1993 | Matzinger et al. | |
| 5,188,966 A | 2/1993 | Eikmeier et al. | 436/170 |
| 5,188,968 A | 2/1993 | Kano et al. | |
| 5,206,177 A | 4/1993 | DeLaCroix et al. | 436/518 |
| 5,207,263 A | 5/1993 | Maier et al. | |
| 5,211,914 A | 5/1993 | Vogel et al. | 422/56 |
| 5,212,060 A | 5/1993 | Maddox | 435/7.1 |
| 5,215,716 A | 6/1993 | Arai | 422/56 |
| 5,217,691 A | 6/1993 | Greene et al. | 422/56 |
| 5,225,997 A | 7/1993 | Lederer et al. | |
| 5,227,310 A | 7/1993 | Sakamoto et al. | 436/469 |
| 5,231,576 A | 7/1993 | Suzuki et al. | |
| 5,246,858 A | 9/1993 | Arbuckle et al. | |
| 5,251,126 A | 10/1993 | Kahn et al. | |
| 5,252,293 A | 10/1993 | Drbal et al. | 422/101 |
| 5,279,294 A | 1/1994 | Anderson et al. | |
| 5,281,395 A | 1/1994 | Markart et al. | |
| 5,296,192 A * | 3/1994 | Carroll et al. | 422/56 |
| 5,302,348 A | 4/1994 | Cusack et al. | |
| 5,304,468 A | 4/1994 | Phillips et al. | |
| 5,316,727 A | 5/1994 | Suzuki et al. | |
| 5,321,492 A | 6/1994 | Detwiler et al. | |
| 5,321,618 A | 6/1994 | Gessman | |
| 5,339,821 A | 8/1994 | Fujimoto | |
| 5,367,555 A | 11/1994 | Isoyama | |
| 5,371,020 A | 12/1994 | Frischauf | |
| 5,379,214 A | 1/1995 | Arbuckle et al. | |
| 5,390,238 A | 2/1995 | Kirk et al. | |
| 5,416,695 A | 5/1995 | Stutman et al. | |
| 5,418,142 A | 5/1995 | Kiser et al. | |
| 5,424,035 A | 6/1995 | Hönes et al. | |
| 5,424,545 A | 6/1995 | Block et al. | |
| 5,431,880 A | 7/1995 | Kramer | |
| 5,452,343 A | 9/1995 | Garland et al. | |
| 5,453,360 A | 9/1995 | Yu | |
| 5,462,051 A | 10/1995 | Oka et al. | |
| 5,467,475 A | 11/1995 | Takahashi et al. | |
| 5,470,752 A | 11/1995 | Burd et al. | |
| 5,515,170 A | 5/1996 | Matzinger et al. | |
| 5,518,689 A | 5/1996 | Dosmann et al. | |
| 5,526,120 A | 6/1996 | Jina et al. | |
| 5,529,755 A | 6/1996 | Higashio et al. | |
| 5,545,877 A | 8/1996 | Shelton | |
| 5,548,633 A | 8/1996 | Kujawa et al. | |
| 5,554,531 A | 9/1996 | Zweig | 435/286.1 |
| 5,563,042 A * | 10/1996 | Phillips et al. | 422/56 |
| 5,573,506 A | 11/1996 | Vasko | |

| Patent Number | Date | Inventor |
|---|---|---|
| 5,576,952 A | 11/1996 | Stutman et al. |
| 5,579,001 A | 11/1996 | Dempsey et al. |
| 5,579,775 A | 12/1996 | Dempsey et al. |
| 5,581,369 A | 12/1996 | Righter et al. |
| 5,597,532 A | 1/1997 | Connolly |
| 5,605,150 A | 2/1997 | Radons et al. |
| 5,605,837 A | 2/1997 | Karimi et al. |
| 5,620,863 A | 4/1997 | Tomasco et al. |
| 5,622,429 A | 4/1997 | Heinze |
| 5,639,672 A | 6/1997 | Burd et al. |
| 5,666,404 A | 9/1997 | Ciccotelli et al. |
| 5,681,529 A | 10/1997 | Taguchi et al. |
| 5,695,949 A | 12/1997 | Galen et al. |
| 5,704,364 A | 1/1998 | Saltzstein et al. |
| 5,704,366 A | 1/1998 | Tacklind et al. |
| 5,715,823 A | 2/1998 | Wood et al. |
| 5,719,034 A | 2/1998 | Kiser et al. |
| 5,725,774 A | 3/1998 | Neyer |
| 5,728,352 A | 3/1998 | Poto et al. |
| 5,735,285 A | 4/1998 | Albert et al. |
| 5,738,828 A * | 4/1998 | Stoughton .................. 422/105 |
| 5,745,308 A | 4/1998 | Spangenberg |
| 5,753,452 A * | 5/1998 | Smith ........................ 422/50 |
| 5,754,111 A | 5/1998 | Garcia |
| 5,755,942 A | 5/1998 | Zanzucchi et al. |
| 5,758,644 A | 6/1998 | Diab et al. .................. 128/633 |
| 5,762,871 A | 6/1998 | Neyer |
| 5,764,158 A | 6/1998 | Franklin et al. |
| 5,770,389 A | 6/1998 | Ching et al. |
| 5,770,839 A | 6/1998 | Ruebush et al. |
| 5,772,586 A | 6/1998 | Heinonen et al. |
| 5,772,963 A | 6/1998 | Cantatore et al. |
| 5,780,304 A | 7/1998 | Matzinger et al. |
| 5,782,878 A | 7/1998 | Morgan et al. |
| 5,785,650 A | 7/1998 | Akasaka et al. |
| 5,791,342 A | 8/1998 | Woodard |
| 5,827,180 A | 10/1998 | Goodman |
| 5,837,546 A | 11/1998 | Allen et al. |
| 5,840,020 A | 11/1998 | Heinonen et al. |
| 5,841,846 A | 11/1998 | Abbruscato |
| 5,842,975 A | 12/1998 | Illyés et al. |
| 5,843,692 A | 12/1998 | Phillips et al. |
| 5,846,486 A | 12/1998 | Pugh |
| 5,850,320 A | 12/1998 | Warmka et al. |
| 5,866,349 A | 2/1999 | Lilja et al. |
| 5,872,627 A | 2/1999 | Miers |
| 5,885,839 A * | 3/1999 | Lingane et al. ............. 436/169 |
| 5,922,530 A | 7/1999 | Yu |
| 5,962,215 A | 10/1999 | Douglas et al. |
| 5,968,760 A | 10/1999 | Phillips et al. ................ 435/14 |
| 5,972,294 A * | 10/1999 | Smith et al. .................. 422/58 |
| 5,986,754 A | 11/1999 | Harding |
| 5,989,917 A | 11/1999 | McAleer et al. |
| 5,995,236 A | 11/1999 | Roth et al. |
| 5,997,817 A | 12/1999 | Crismore et al. |
| 6,027,692 A | 2/2000 | Galen et al. |
| 6,032,352 A | 3/2000 | Furay et al. |
| 6,040,195 A * | 3/2000 | Carroll et al. ................ 422/55 |
| 6,067,463 A | 5/2000 | Jeng et al. |
| 6,069,011 A * | 5/2000 | Riedel .................... 422/82.01 |
| 6,084,660 A | 7/2000 | Shartle |
| 6,150,124 A * | 11/2000 | Riedel ........................ 435/14 |
| 6,168,957 B1 | 1/2001 | Matzinger et al. |
| 6,193,873 B1 | 2/2001 | Ohara et al. |
| 6,201,607 B1 | 3/2001 | Roth et al. |
| 6,226,082 B1 | 5/2001 | Roe |
| 6,233,471 B1 | 5/2001 | Berner et al. |
| 6,268,162 B1 | 7/2001 | Phillips et al. ................ 435/14 |

FOREIGN PATENT DOCUMENTS

| | | |
|---|---|---|
| EP | 0 110 173 | 6/1984 |
| EP | 0 112 166 | 6/1984 |
| EP | 0 113 896 | 7/1984 |
| EP | 0 133 481 | 2/1985 |
| EP | 0 140 337 | 5/1985 |
| EP | 0 141 648 | 5/1985 |
| EP | 0 159 727 | 10/1985 |
| EP | 0 166 878 | 1/1986 |
| EP | 0 169 055 | 1/1986 |
| EP | 0 173 500 | 3/1986 |
| EP | 0 174 247 | 3/1986 |
| EP | 0 182 647 | 5/1986 |
| EP | 0 183 524 | 6/1986 |
| EP | 0 225 561 A3 | 12/1987 |
| EP | 0 256 806 | 2/1988 |
| EP | 0 271 854 | 6/1988 |
| EP | 0 295 526 | 12/1988 |
| EP | 0 336 483 | 10/1989 |
| EP | 0 345 781 | 12/1989 |
| EP | 0 407 800 | 6/1990 |
| EP | 0 414 563 | 2/1991 |
| EP | 0 415 679 | 3/1991 |
| EP | 0 473 241 | 3/1992 |
| EP | 0 475 692 | 3/1992 |
| EP | 0 479 394 | 4/1992 |
| EP | 0 511 120 | 10/1992 |
| EP | 0 555 045 | 8/1993 |
| EP | 0 574 134 | 12/1993 |
| EP | 0 735 369 | 3/1995 |
| EP | 0 656 423 | 7/1995 |
| EP | 0 759 555 | 8/1995 |
| EP | 0 769 558 | 10/1995 |
| EP | 0 779 367 | 12/1995 |
| EP | 0 800 082 | 4/1996 |
| EP | 0 764 271 | 3/1997 |
| EP | 0 779 984 | 6/1997 |
| EP | 0 781 405 | 7/1997 |
| EP | 0 781 406 | 7/1997 |
| EP | 0 799 896 | 10/1997 |
| EP | 0 816 849 | 1/1998 |
| EP | 0 823 634 | 2/1998 |
| EP | 0 823 635 | 2/1998 |
| EP | 0 823 636 | 2/1998 |
| EP | 0 826 777 | 3/1998 |
| EP | 0 832 691 | 4/1998 |
| EP | 0 852 336 | 7/1998 |
| EP | 0 960 946 | 12/1999 |
| EP | 0 974 840 | 1/2000 |
| FR | 2191734 | 2/1974 |
| GB | 835551 | 5/1960 |
| GB | 911181 | 11/1962 |
| GB | 1037155 | 7/1966 |
| GB | 1485506 | 9/1977 |
| GB | 2029012 | 3/1980 |
| GB | 2026160 | 6/1980 |
| GB | 2039035 | 7/1980 |
| GB | 2090659 | 7/1982 |
| JP | 49-11395 | 1/1974 |
| JP | 53-148522 | 12/1978 |
| JP | 54-113383 | 9/1979 |
| JP | 55-136957 | 10/1980 |
| JP | 55-155235 | 12/1980 |
| JP | 56-057937 | 5/1981 |
| JP | 56-164941 | 12/1981 |
| JP | 56-168148 | 12/1981 |
| JP | 57-101760 | 6/1982 |
| JP | 57-163848 | 10/1982 |
| JP | 57-168144 | 10/1982 |
| JP | 58-021544 | 2/1983 |
| JP | 59-032850 | 2/1984 |
| JP | 59-032851 | 2/1984 |
| JP | 59-108942 | 6/1984 |

| | | |
|---|---|---|
| JP | 59-182347 | 10/1984 |
| JP | 60-091265 | 5/1985 |
| JP | 61-026842 | 2/1986 |
| JP | 61-068539 | 4/1986 |
| JP | 61-155849 | 7/1986 |
| JP | 61-292540 | 12/1986 |
| JP | 62-22066 | 1/1987 |
| JP | 62-298765 | 12/1987 |
| JP | 63-021558 | 1/1988 |
| JP | 63-175749 | 7/1988 |
| JP | 1-119743 | 1/1989 |
| JP | 7-311196 | 7/1995 |
| JP | 8-75735 | 3/1996 |
| SU | 172088 | 12/1965 |
| WO | 81/00622 | 3/1981 |
| WO | 81/00912 | 4/1981 |
| WO | 83/00931 | 3/1983 |
| WO | 84/02578 | 7/1984 |
| WO | 92/12428 | 7/1992 |
| WO | 92/15861 | 9/1992 |
| WO | 94/02578 | 2/1994 |
| WO | 96/07757 | 3/1996 |
| WO | 96/07892 | 3/1996 |
| WO | 96/07893 | 3/1996 |
| WO | 96/07907 | 3/1996 |
| WO | 96/07908 | 3/1996 |
| WO | 97/46878 | 12/1997 |
| WO | 99/46591 | 9/1999 |

OTHER PUBLICATIONS

Adlercreutz, H. et al., "Evaluation of the New System Olli 3000 Kinetic Ultraviolet Analyzer for Measuring Aspartate and Alanine Aminotransferase and Lactate Dehydrogenase Activities in Serum," Clinical Chemistry, vol. 21, No. 6, pp. 676–84 (1975).

Al–Kaissi, E. et al., "Assessment of Subtrates for Horseradish Peroxidase in Enzyme Immunoassay," Journal of Immunological Methods, 58, pp. 127–132 (1983).

Article (ECRI): "Blood Glucose Monitors," Health Devices, vol. 17, No. 9, pp. 253–271 (Sep. 1988).

Bandi, Z.L. et al., "Extended Clinical Trial and Evaluation of Glucose Determination with the Eastman Kodak Ektachem GLU/BUN Analyzer," Clinical Chemistry, vol. 27, No. 1, pp. 27–34 (1981).

Bell, P.M. et al., "Benefits of Self Monitoring of Blood Glucose," British Medical Journal, vol. 286, pp. 1230–1231, Apr. 16, 1983.

Billmeyer, F.W. Jr., et al., Principles of Color Technology, Second Edition, John Wiley & Sons, Inc. 1981.

Bio–Dynamics Corp.,"Coagulation Unimeter CU500 Series Technical Service Manual," Nov., 1982.

Capaldi, Dante J. et al., "A New Peroxidase Color Reaction: Oxidative Coupling of 3–Methyl–2–Benzothiazolinone Hydrazone (MBTH) with its Formaldehyde Azine Application to Glucose and Choline Oxidases," Analytical Biochemistry, 129, 329–336 (1983).

Carrick, C.E., "Barriers to Performance of Maintenance and Quality Control (QC) by Patients Using Home Glucose Meters," Diabetes, May 1990, vol. 39, Supp. 1, The Program for the 50th Annual Meeting of the American Diabetes Association in Atlanta, Georgia, Abstract #205.

Cate, J.C. IV, "Evaluation of an Engineering Model of the 'Ektachem' Analyzer for Glucose and Urea Assay," Clinical Chemistry, vol. 26, No. 2, p. 266 (1980).

Chance, B., "Rapid and Sensitive Spectrophotometry. III. A Double Beam Apparatus," Rev. Sci. Instru., 22, pp. 634–638 (1951).

Chua, K.S., et al., "Plasma Glucose Measurement with the Yellow Springs Glucose Analyzer," Clinical Chemistry, vol. 24, No. 1, pp. 150–152 (1978).

Cohen, M. et al., "Home Blood–Glucose Monitoring—A New approach to the Management of Diabetes Mellitus," Med. J. Aust. 1980; 2: 713–716.

Cohen, Matthew et al., "Self–Monitoring of Blood Glucose Levels in Non–Insulin–Dependent Diabetes Mellitus," Med. J. Aust. 1983; 2: 377–380.

Cowles, J.C., "Theory of Dual–Wavelength Spectrophotometry for Turbid Samples," Journal of the Optical Society of America, vol. 55, No. 6, pp. 690–693, Jun. 1965.

Curme, H.G., et al., "Multilayer Film Elements for Clinical Analysis: General Concepts," Clinical Chemistry, vol. 24, No. 8, pp. 1335–1342 (1978).

Damon Corporation, "Instrument Operating Parameters –Damon Microfluorometer," (no date available).

Davidson, J.A., et al., "Evaluation of a New Blood Glucose Meter and Test Strip Intended for Hospital Bedside Glucose Testing," Diabetes, May 1990, vol. 39, Supp. 1, The Program for the 50th Annual Meeting of the American Diabetes Association in Atlanta, Georgia, Abstract #871.

De Pasqua, A., et al., "Errors in Blood Glucose Determination," The Lancet, p. 1165 (1984).

Driscoll, R.C., et al., "Discrete Automated Chemistry System with Tableted Reagents," Clinical Chemistry, vol. 29, No. 9, pp. 1609–1615 (1983).

Eastman Kodak Co., "DT60 Analyzer Operator's Manual," Pub. No. C–50, Part No. 632071, Jul. 1986.

Eastman Kodak Co., "Kodak Ektachem DT Slides: (GLU) –Glucose Test Methodology," Pub. No. C–300, Copyright 1986.

Eastman Kodak Co., "Kodak Ektachem DT Slides—Test Methodology –Glucose," Pub. No. C–300 (1992).

Eastman Kodak Co., "Normal Operation for the Kodak Ektachem DTSC Module," Pub. No. XP3100–5, Sep. 1991.

Elliott, R. J., "Ektachem DT60 Analyzer," Physicians & Computers vol. 2, No. 6, pp. 13–16 (Oct. 1984).

European Patent Office Opposition File, European Patent 0 256 806, granted on Application No. 873–7014.8, Lifescan, Inc., Opposition by Boehringer Mannheim GmbH.

Evenson, M.A., et al., "Peak Characteristics and Computers in Continuous Flow Analysis," Clinical Chemistry, vol. 16, No. 7, pp. 606–611 (1970).

Fairclough et al., "An Evaluation Of Patient Performance Of and Their Satisfaction With Various Rapid Blood Glucose Measurement Systems," Diabetes Care, vol. 6, No. 1, pp. 45–49 (1981).

Feldman, J.M. et al., "Inhibition of Glucose Oxidase Paper Tests by Reducing Metabolites," Diabetes, vol. 19, No. 5, pp. 337–343 (May, 1970).

Finley, P.R. et al., "Evaluation of a New Multichannel Analyzer," Clinical Chemistry, vol. 24, No. 12, p. 2126 (1978).

Fleming, D.R., "Who Benefits from Automatic Record Keeping," Diabetes, May 1990, vol. 39, Supp. 1, The Program for the 50th Annual Meeting of the American Diabetes Association in Atlanta, Georgia, Abstract #862.

Funnell, M.M., et al., "Perceived Effectiveness, Cost and Availability of Patient Education Methods and Materials," Diabetes, May 1990, vol. 39, Supp. 1, The Program for the 50th Annual Meeting of the American Diabetes Association in Atlanta, Georgia, Abstract #200.

Geoghegan, W.D. in "Enzyme–Mediated Immunoassay," Ngo and Lenhoff, ed., pp. 451–465 (1985).

Geoghegan, W.D. et al., "Adaptation of the Ngo–Lenhoff Peroxidase Assay for Solid Phase ELISA," Journal of Immunological Methods, 60, pp. 61–68 (1983).

Gilden, J.L., et al., "Matchmaker: A Visual Reader Improves Monitoring Accuracy, Quality of Life and Glycemic Control in Elderly Diabetics," Diabetes, May 1990, vol. 39, Supp. 1, The Program for the 50th Annual Meeting of the American Diabetes Association in Atlanta, Georgia, Abstract #868.

Hahn B., et al., "Polychromatic Analysis: New Applications of an Old Technique," Clinical Chemistry, vol. 25, No. 6, pp. 951–959 (1979).

Hardin, E., et al. "Clinical Laboratory Evaluation of the Perkin–Elmer KA–150 Enzyme Analyzer," Clinical Chemistry, vol. 22, No. 4, pp. 434–438 (1976).

Havlin, C.E., et al., "Critical Evaluation of Blood Glucose Monitoring Devices," Diabetes, May 1990, vol. 39, Supp. 1, The Program for the 50th Annual Meeting of the American Diabetes Association in Atlanta, Georgia, Abstract #873.

"Healthcare Product Comparison System (HCPS): Blood Glucose Monitors," ECRI, 35 pp. (1999).

Ikeda, Y. et al., "Pilot Study of Self–Measurement of Blood Glucose Using the Dextrostix–Eyetone System for Juvenile–Onset Diabetes," Diabetologia, 15, pp. 91–93 (1978).

Jarrett, L., et al., "Home Blood Glucose Meters with Memories," Diabetes, May 1990, vol. 39, Supp. 1, The Program for the 50th Annual Meeting of the American Diabetes Association in Atlanta, Georgia, Abstract #685.

Keilin, D., "Properties of Glucose Oxidase (Notatin)," Biochem., 42, pp. 221–229 (1948).

Kineiko, R.W., et al., "Laboratory Evaluation of the Boehringer Mannheim 'Hitachi 705' Automatic Analyzer," Clinical Chemistry, vol. 29, No. 4, p. 688 (1983).

Lee, E.Y., et al., "Do Physicians Appropriately Utilize Inpatient Bedside Glucose Monitoring?," Diabetes, May 1990, vol. 39, Supp. 1, The Program for the 50th Annual Meeting of the American Diabetes Association in Atlanta, Georgia, Abstract #883.

Leroux et al., "Ward Level Evaluation Of The 'One Touch' Glucose Meter," Clin. Chem., vol. 34 No. 9, 1988, p. 1928.

Lo, D.H. et al., "Quantitative Estimate of Total Bilirubin in Serum Using the *Kodak Ektachem*Clinical Chemistry Slide," Clinical Chemistry, vol. 30, No. 6, p. 970 (1984).

Lo, D.H. et al, "Quantitative Estimate of Total Bilirubin in Serum Using the Kodak Ektachem Clinical Chemistry Slide (TBIL)," Jul. 31, 1984, (Copyright 1984 Eastman–Kodak).

Medical Laboratory Automation Inc., "Pipette Care and Procedure Manual," (Copyright 1983).

Miles Laboratories, "Seralyzer Operating Manual," (Revised Jan./1984) including Test Module Inserts (Various revision dates) and Dilution System Instructions (Various revision dates).

Miles Laboratories, "Seralyzer Reflectance Photometer Assay Procedures in Brief" (Revised Aug./1984).

Morgenstern, Stan et al., "STAC Rate Reaction and Fixed–Point Methods," pp. 16–22, Dec. 1976.

Morris, D.L. et al., "A Chemistry for the Immobilization of Enzymes on Nylon," Biochem. J., vol. 147(3), pp. 593–603 (1975).

Murkin, S.A., et al., "Anchored Instruction (AI) Enhances Diabetes (DM) Problem Solving," Diabetes, May 1990, vol. 39, Supp. 1, The Program for the 50th Annual Meeting of the American Diabetes Association in Atlanta, Georgia, Abstract #65.

Neeley, E. et al., "An Instrument for Digital Matrix Photometry," in Nipper, H. (ed), "Selected Papers on Cliniical Chemistry Instrumentation", AACC Press, Washington, pp. 35–38 (1985).

Neeley, E. et al., "Reflectance Digital Matrix Photometry," in Nipper, H. (ed), "Selected Papers on Cliniical Chemistry Instrumentation", AACC Press, Washington, pp. 39–42 (1985).

Neeley, W., et al., "Design and Operation of a Signal Comparator to Increase Efficiency of Continuous–Flow Analyzers," in Nipper, H. (ed), "Selected Papers on Cliniical Chemistry Instrumentation", AACC Press, Washington, pp. 150–152 (1985).

Neeley, W., et al., "Design and Performance of a Miniaturized High–Speed Continuous–Flow Analyzer," in Nipper, H. (ed), "Selected Papers on Cliniical Chemistry Instrumentation", AACC Press, Washington, pp. 153–156 (1985).

Neeley, W., et al., "High–Performance'Colorimeter with an Electronic Bubble Gate for Use in Miniaturized Continuous–Flow Analyzers," in Nipper, H. (ed), "Selected Papers on Cliniical Chemistry Instrumentation", AACC Press, Washington, pp. 157–161 (1985).

Neely, W. et al., "Multilayer Film Analysis for Glucose in 1–microliter Samples of Plasma," Clinical Chemistry 29/12, pp. 2103–2105 (1985).

Ngo, T.T., et al., "A Sensitive and Versatile Chromogenic Assay for Peroxidase and Peroxidase–Coupled Reactions," Analytical Biochemistry, 105, pp. 389–397 (1980).

Ohkubo et al., "Plasma Glucose Concentrations Of Whole Blood, As Determined With A Multilayer–Film Analytical Element," Clinical Chemistry, vol. 27, No. 7, (1981) pp. 1287–1290.

Passey, R. et al., "Measurement of Spectral Bandwidth, as exemplified with the 'Beckman Enzyme Analyzer System TR'Spectrophotometer," Clinical Chemistry, vol. 21, No. 11, pp. 1582–84 (1975).

Passey, R., et al., "Evaluation of the Beckman 'System TR Enzyme Analyzer'," Clinical Chemistry, vol. 21, No. 8, pp. 1107–1112 (1975).

Passey, R., et al., "Measurement of Spectral Bandwidth as Exemplified with the Beckman 'Enzyme Analyzer System TR Spectrophotometer'," in Nipper, H. (ed), "Selected Papers on Cliniical Chemistry Instrumentation", AACC Press, Washington, pp. 39–42 (1985).

Pellegrino, L.S., et al., "Pilot study: Blood Glucose Monitors," Diabetes, May 1990, vol. 39, Supp. 1, The Program for the 50th Annual Meeting of the American Diabetes Association in Atlanta, Georgia, Abstract #882.

Percy–Robb, I.W., et al., "The Peak Monitor of the Technicon SMAC System," Clinical Chemistry, vol. 24, No. 1, pp. 146–148 (1978).

Polesello A. et al., "Application of Near Infra Red Spectrophotometry to the Nondestructive Analysis of Foods: A Review of Experimental Results," CRC Critical Reviews In Food Science and Nutrition 18(3): 203–30 (1983).

Rachlin, J.A., et al., "User Errors in Blood Glucose Monitoring," Diabetes, May 1990, vol. 39, Supp. 1, The Program for the 50th Annual Meeting of the American Diabetes Association in Atlanta, Georgia, Abstract #879.

Ratzlaff, K.L. et al., "Theoretical Assessment of Precision in Dual Wavelength Spectrophotometric Measurement," Analytical Chemistry, vol. 49, No. 14, pp. 2170–2176, Dec. 1977.

Richards, F.M. et al., "Glutaraldehyde as a Protein Cross–linking Reagent," J. Mol. Biol., 37, pp. 231–233 (1968).

Rikmenspoel, Robert, "The Sensitivity and Accuracy of Dual–Wavelength Spectrophotometers," Applied Optics, vol. 3, No. 3, pp. 351–355, Mar. 1964.

Schocken, D.M., et al., "Marketing Diabetes Education Reaches Primary Care Physicians," Diabetes, May 1990, vol. 39, Supp. 1, The Program for the 50th Annual Meeting of the American Diabetes Association in Atlanta, Georgia, Abstract #66.

Scott, W.E., "Filler Research Studies Improve Papermaking Applications," American Papermaker, pp. 12–14, May 1987.

Shibata, Shozo et al., "Dual–Wavelength Spectrophotometry—Part 1. General Method," Analytica Chimica Acta, 46, pp. 271–279 (1969).

Shirey, T.L., "Development of a Layered–Coating Technology for Clinical Chemistry," Clinical Biochemistry, vol. 16, No. 2, pp. 147–155, 1983.

Shoucri, R,M., et al., "Some Observations on the Kinetics of the Jaffe Reaction for Creatinine," Clinical Chemistry, vol. 23, No. 9, pp. 1527–1530 (1977).

Smith, J., et al., "An Innovative Technology for 'Random–Access'Sampling," in Nipper, H. (ed), "Selected Papers on Cliniical Chemistry Instrumentation", AACC Press, Washington, pp. 193–197 (1985).

Sodickson, L., Presentation Slides (1976–1977).

Soloniewicz, R. et al., "Spectrophotometric Determination of Reducing Sugars with Aromatic Nitro Compounds," Institute of General Chemistry, Technical University, Lodz, Poland, pp. 105–114 (1980).

Songer, T.J., "Health Insurance Characteristics in Families with IDDM Children," Diabetes, May 1990, vol. 39, Supp. 1, The Program for the 50th Annual Meeting of the American Diabetes Association in Atlanta, Georgia, Abstract #210.

Sönksen, P.H. et al., "Home Monitoring of Blood–Glucose—Method for Improving Diabetic Control," The Lancet, vol. 1978:1, No. 8067, pp. 729–732 (Apr. 8, 1978).

Spayd, R.W., et al., "Multilayer Film Elements for Clinical Analysis: Applications to Representative Chemical Determinations," Clinical Chemistry, vol. 24, No. 8, pp. 1343–1350 (1978).

Sternberg, J.C. et al., "Spectrophotometric Analysis of Multicomponent Systems Using the Least Squares Method in Matrix Form: The Ergosterol Irradiation System," Analytical Chemistry, vol. 32, No. 1, Jan. 1960, pp. 84–90.

Sundaram et al., "Routine Glucose Determination In Serum By Use Of An Immobilized Glucose Dehydrogenase Nylon–Tube Reactor," Clinical Chemistry, vol. 25, No. 8, (1979) pp. 1436–1439.

Table: "Effects of Sample Volume and Anticoagulant on Ekatchem Accuracy," Clinical Chemistry, vol. 27, No. 1, p. 33 (1981).

Tideman, A.M., "Clinical Evaluation of a Hospital Blood Glucose Monitoring System," Diabetes, May 1990, vol. 39, Supp. 1, The Program for the 50th Annual Meeting of the American Diabetes Association in Atlanta, Georgia, Abstract #877.

Tietz, N. (ed.), "Ektachem 700" in Textbook of Clinical Chemistry, (Philadelphia: W.B. Saunders Company) 1986, pp. 267–269.

Tietz, N.(ed.), "Methods for the Determination of Glucose in Body Fluids" in Fundamentals of Clinical Chemistry, (Philadelphia: W.B. Saunders Company) 1976, pp. 242–243.

TOA Technical Journal (1972) No. 3, pp. 2–9, "Royco–TOA Model 910 Cell Counter" (Japanese).

Toren, E.C. Jr., et al., "Interface Instrumentation between Computer and Spectrophotometer for Reaction Rate Measurements," Clinical Chemistry, vol. 16, No. 3, pp. 215–221 (1970).

Villeneuve, M.E. et al., "Evaluating Blood Glucose Monitors," American Journal of Nursing, Nov. 1985, pp. 1258–1259.

Walford, S. et al., "Self–Monitoring of Blood–Glucose—Improvement of Diabetic Control," The Lancet, pp. 732–735, Apr. 8, 1978.

Walker, E.A., et al., "What is the Present Practice of Quality Assurance for Bedside BGM in Health Care Facilities?," Diabetes, May 1990, vol. 39, Supp. 1, The Program for the 50th Annual Meeting of the American Diabetes Association in Atlanta, Georgia, Abstract#872.

Walter, B., "Dry Reagent Chemistries in Clinical Analysis," Analytical Chemistry, vol. 55, No. 4, Apr. 1983, pp. 498A–514A.

Wilkman, M.J., "Evaluation of Nurse Accuracy of Bedside Glucose Monitoring with Two Systems," Diabetes, May 1990, vol. 39, Supp. 1, The Program for the 50th Annual Meeting of the American Diabetes Association in Atlanta, Georgia, Abstract #682.

Wing, R.R., et al., "Behavioral Skills in Self–Monitoring of Blood Glucose: Relationship to Accuracy" Diabetes Care, vol. 9, No. 4, Jul., Aug. 1986, pp. 330–333.

Wylie–Rosett, J., et al., Brief Diabetes Quality Assurance (QA) Checklist,38 Diabetes, May 1990, vol. 39, Supp. 1, The Program for the 50th Annual Meeting of the American Diabetes Association in Atlanta, Georgia, Abstract#866.

Zamzow, K., et al., "New Wearable Continuous Blood Glucose Monitor (BGM) and Artificial Pancreas (A)," Diabetes, May 1990, vol. 39, Supp. 1, The Program for the 50th Annual Meeting of the American Diabetes Association in Atlanta, Georgia, Abstract #20.

Zimmet, P. et al., "Computerized Assessment of Self–Monitored Blood Glucose Results Using a Glucometer Reflectance Photometer with Memory and Microcomputer," Diabetes Research and Clinical Practice, pp. 55–63 (1985).

Zollinger, H., "The Mechanism of Oxidative Coupling," Azo and Diazo Chemistry Aliphatic and Aromatic Compounds, 1961, pp. 243–248.

Kessler, G., et al., "Biochromatic Analysis As Applied To The Technicon STAC Biochemical Analyzer," Chem. Abstr., vol. 89, No. 13, p. 357 (1978).

Przybylowicz, E. P., et al., "A New Technology for the Clinical Laboratory," Clinical Chemistry, vol. 24, No. 6, p. 1008 (1978).

Reynolds, K. J. et al., "Temperature Dependence of LED and Its Theoretical Effect on Pulse Oximetry," Brit. J. Anaesth. 1991; 67: 638–643.

* cited by examiner

METHOD FOR DETERMINING CONCENTRATION OF AN ANALYTE IN A TEST STRIP

DESCRIPTION OF THE INVENTION

1. Field of the Invention

The present invention relates generally to methods of measuring the concentration of an analyte in a fluid sample. More particularly, this invention provides methods for determining the appropriate point at which to take a measurement of an analyte concentration in a fluid sample applied to a test strip.

2. Background of the Invention

Monitoring analytes such as glucose, cholesterol, intoxicants, and other constituents is frequently desirable in fluids, such as blood, plasma, blood serum, saliva, urine, and other biological fluids. In healthcare applications, such monitoring affords the opportunity to make rapid diagnoses of a patient's condition and to take prophylactic or therapeutic measures necessary for maintaining proper health.

One such healthcare application that has benefited tremendously by analyte monitoring in recent years is the treatment of diabetes. Diabetics suffer from an impaired ability to regulate glucose levels in their blood. As a result, diabetics can have abnormally high blood sugar levels known as hyperglycemia. Chronic hyperglycemia may lead to long-term complications such as cardiovascular disease and degeneration of the kidneys, retinas, blood vessels and the nervous system. To minimize the risk of such long term complications, diabetics must strictly monitor and manage their blood glucose levels.

Diabetics that have glucose levels that fluctuate several times throughout the day require very close blood glucose level monitoring. Close monitoring of blood glucose levels is most easily obtained when a diabetic is able to monitor their glucose levels themselves. Many devices currently available allow diabetics to measure their own blood sugar levels.

Reflectance-based monitors comprise one category of personal, or home-use, glucose level monitoring devices. These monitors utilize an optical block which accepts test elements for photometric analysis.

The test elements are usually in the form of test strips, which contain analytical chemistry. Conventionally, these test strips are in the form of a disposable diagnostic test strip containing analytical chemistry upon which a fluid sample is deposited. Once the user applies the fluid sample to the test strip, and the sample has sufficiently penetrated the test strip, a chemical reaction occurs in the presence of a target analyte, e.g., glucose, to cause a change in the optical properties of the test strip. An optical photometric device then determines the analyte level of the sample by measuring an optical property, such as the intensity of reflected light at a certain wavelength from the test strip. For in vitro analysis in healthcare applications, the fluid sample is usually fresh whole blood. Periodically, however, it is desirable to run a test on a test element formed by applying a control solution of known analyte concentration to a test strip, in order to verify that the meter is performing within operational limits. It is also desirable for the user to insert a "standard strip", which is a test element that has known optical properties, in order to verify that the meter is operating within operational limits.

Diagnostic test strips for testing analytes such as glucose levels of blood samples are well known in the art and comprise various structures and materials. Test strips typically include single or multi-layered porous membrane arrangements which receive a blood sample and undergo a change in an optical property, such as a color change, in response to the interaction of blood glucose with agents/reactants in the membrane. Examples of such multi-layer strips are described in U.S. Pat. No. 5,296,192 to Carroll and U.S. Pat. No. 6,010,999 to Carroll et al., the contents of both of which are incorporated herein by reference.

Prior to reaching the reactants, a whole blood sample can be filtered to eliminate potential optical interference by removing erythrocytes, or red blood cells. Some test strips operate to allow the applied blood sample to migrate to a reaction site in the membrane where the sample reacts with the agents/reactants, which is located in downstream capillary relation to the sample application site. The results of the reaction are often visible as a color change at the reaction site. However, the change may occur in invisible regions of the electromagnetic spectrum, such as infrared and ultraviolet. For the purposes of this application, the term "color change" will be understood to include variations in optical properties throughout the visible and invisible regions of the electromagnetic spectrum. As noted above, a color change can be correlated to the amount of glucose in the sample. Home-use glucose measuring devices that use a reflectance meter to measure the color change of the test strip correlate glucose levels to the change in the amount of light reflected from the reaction site of the test strip. As is well known in the art, strips can be formulated to produce a color change within a certain spectral region, and the meter designed to photometrically measure reflected, absorbed or transmitted light at a wavelength sensitive to the color change of the strip. While the present invention will be described with reference to reflectance based photometry, it would be known to one having ordinary skill in the art to apply the features of the invention to absorbance or transmittance based systems.

An important aspect to the accurate measurement of glucose levels in a fluid using a test strip are the methods used to calculate the glucose concentration values from the reflectance values obtained. Because different samples physically vary and will contain different levels of analyte, reaction rates and durations will vary. Prior art devices have focused on fixing an initiation point, the time from which the monitoring device begins to measure the chemical reaction of the blood sample with the test strip. This initiation point often was carefully tied to the initial contact of analyte and reagent, either manually or automatically and then the reaction was timed for a fixed period of time from this initiation point. The end point is the time at which the monitoring device takes a final reflectance reading to calculate the reported glucose level of the sample from calibration data stored in the meter's memory. Because a fixed time (or times) is used in the prior art, calibration is simplified, but this approach requires waiting for a fixed period. The fixed time period is usually longer than required for the reaction to complete, resulting in user inconvenience.

Some home-use glucose monitoring devices have an initiation point corresponding to manual, or user determined events. For example, some monitoring devices trigger the initiation point for measuring glucose levels upon the pressing of a button, the insertion of a test strip into the monitoring device, or upon closing an element, such as a cover or door, of the monitoring device over the test strip. These user-defined initiation points decrease the accuracy and consistency of the monitoring device because they rely on the inconsistent timing of an action by the user (i.e. insertion or covering of the test strip in the monitoring device). These inaccuracies in determining the initiation point are commonly carried through to the end point measurement time. This results from the fact that many common monitoring devices use a fixed time period from the initiation point to determine when to initiate the end point measurement. This fixed period timing is especially problematic when using multi-layer test strips because of the nonuniform absorption periods inherent with such test strips, owing to physical differences between various samples (e.g. hematocrit, sample viscosity as well as general operational conditions such as temperature, humidity, etc.).

Accordingly, conventional methods for determining initiation and end points for measuring glucose levels from test strips may yield inaccurate results because the methods depend on events or time periods unrelated to the reaction kinetics of the blood sample and the test strip. Further, because reactions each occur at different rates, reliance on a fixed time period between an initiation point and the end point may prolong the measuring time beyond the time necessary to accurately measure the glucose level of the sample, resulting in user inconvenience. While a more accurate measuring time may only yield a few seconds improvement over a fixed measuring time, such an improvement is substantial to the person who uses a device multiple times daily. Further, a more accurate, uncomplicated and quick method for testing blood samples for glucose levels will encourage patients to monitor their blood sugar levels more regularly, thereby promoting compliance with their prescribed regimens for diabetes management.

It is accordingly a primary object of the invention to provide a method for rapid and accurate methods for determining an analyte concentration in a fluid sample.

SUMMARY OF THE INVENTION

In accordance with the invention, a method is disclosed for measuring an analyte in a fluid sample in a meter system, comprising the steps of: a) initiating a measuring period for a fluid sample; b) measuring a property of the fluid sample at each of n points in time, said multiple points in time being spaced at predetermined intervals to form a sequence of n measurement values, where n is an integer; c) comparing two nonconsecutive measurement values to determine at least one ratio; d) terminating the measuring of the fluid sample when at least one of said at least one ratio meets predetermined criteria indicating a final analyte value can be accurately determined; and e) determining a final analyte value based on said measurement values.

In further accordance with the invention, a meter system is disclosed for measuring an analyte in a fluid sample, comprising: a light intensity control circuit for measuring reflectance values of an analytic test strip onto which a fluid sample has been applied; and a processor for (a) initiating a measuring period for a fluid sample; (b) measuring the reflectance of a portion of the test strip onto which the fluid sample has been applied at each of n points in time, said multiple points in time being spaced at predetermined intervals to form a sequence of n calculated measurement values, where n is an integer; (c) comparing two nonconsecutive measurement values to determine at least one ratio; (d) terminating the reflectance measuring when at least one of said at least one ratio meets predetermined criteria indicating a final analyte value can be accurately determined; and (e) determining a final analyte value based on said measurement values; and a display for reporting said final analyte value in a user comprehensible format.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, describe an illustrative embodiment of the invention and together with the description, serve to explain the principles of the invention.

DESCRIPTION OF AN ILLUSTRATIVE EMBODIMENT

Reference will now be made in detail to an illustrative embodiment of the invention, an example of which appears in the accompanying drawings. Wherever possible, the same reference numbers will be used throughout the drawings to refer to the same or like parts.

Figure 1:
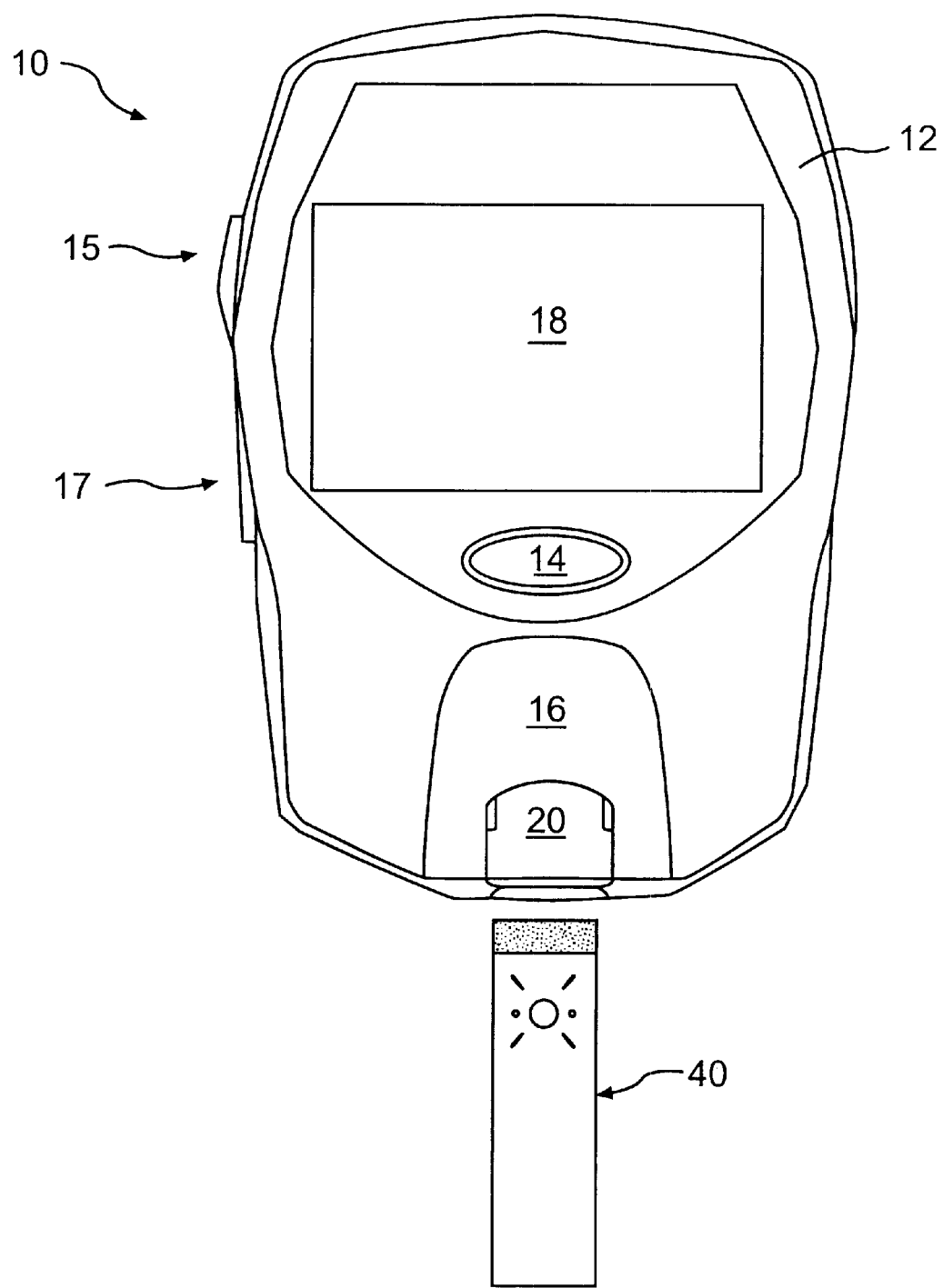
FIG. 1 is a perspective view of an analyte meter system according to an illustrative embodiment of the present invention.

With reference to the drawings, FIG. 1 depicts an analyte meter system 10 according to the present invention. Meter system 10 generally includes a hand-held meter having a housing enclosure 12, power switch/button 14, up/down menu navigation button 15, menu select button 17, liquid crystal display (LCD) 18, and removable test chamber cover or shroud 16 having a test strip platform 20 for receiving and testing a multi-layered diagnostic test strip 40 for the amount of a suspected analyte, such as glucose, cholesterol, ketones, theophylline, fructosamine, and others. A strip sensor (not shown) of known configuration is located at a distal end of the strip platform 20 to detect when a test strip 40 has been fully inserted into the device. Although the discussion is directed herein to an illustrative embodiment of monitoring glucose levels in whole blood samples for purposes of describing the instant invention, one having ordinary skill in the art will appreciate that the present invention is adaptable for testing any of a plurality of analytes.

Figure 2:
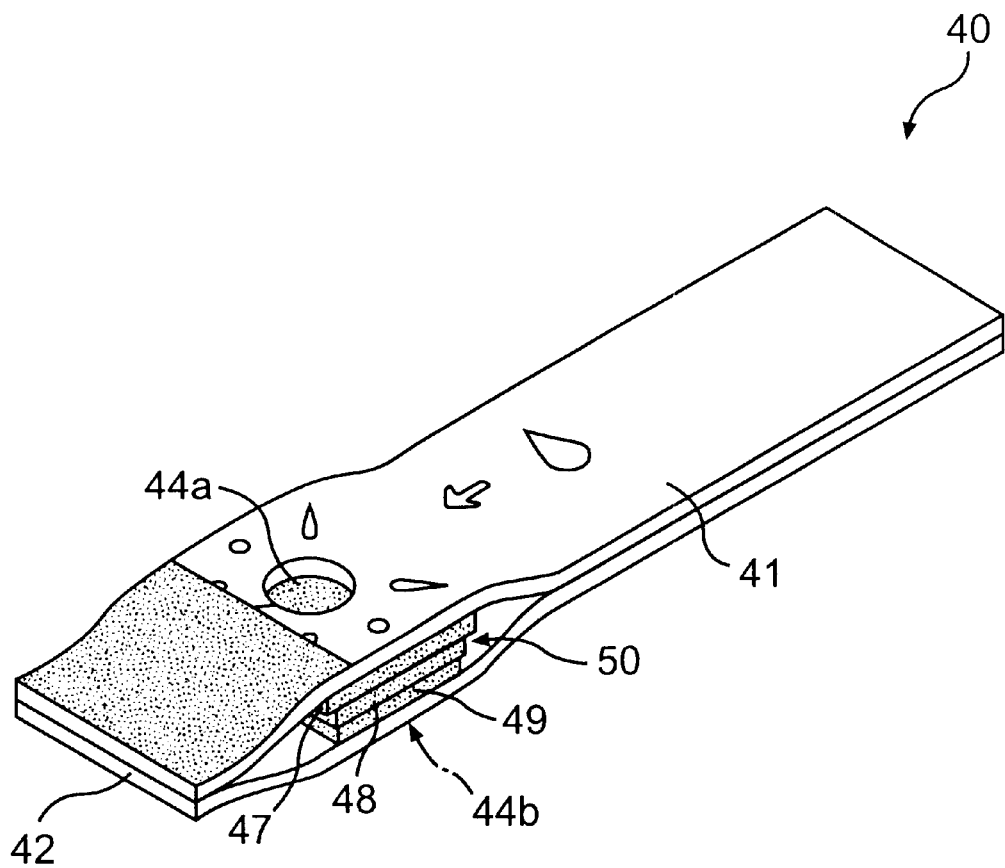
FIG. 2 is a test strip for receiving test fluid according to an illustrative embodiment of the present invention.

FIG. 2 illustrates an enlarged view of a representative diagnostic test strip 40. Test strip 40 generally includes an upper and lower support layer 41, 42, with sample receiving layers 50 located between the support layers. Sample receiving layers 50 include a spreading layer 47 located adjacent upper support layer 41, a separating layer 48, and a semi-porous membrane reagent layer 49 located adjacent lower support layer 42. At least one of the sample receiving layers 50 is pretreated with a dry chemistry reagent and conditioning solution. Preferably, the membrane 49 and separating layer 48 are pretreated with the reagent/conditioning solution. The spreading layer 47 may also be treated. Each layer is positioned in substantially continuous contact with its adjacent layer as shown in FIG. 2 by adhesives and ultrasonic bonding or other known means to provide a sealed composite structure.

The top and bottom support layers 41, 42 of test strip 40 each define an aperture or opening therethrough. These apertures or openings of the test strip are oriented in vertical alignment with test window of the meter (not shown) located along the strip platform. when properly positioned in meter system 10. The opening in the upper support strip 41 defines a sample receiving port 44a and the opening in the lower support strip defines a reaction viewing port 44b. The sample receiving layers 50 are oriented in vertical alignment with sample receiving port 44a and reaction viewing port 44b. This allows the blood sample received by the strip to pass directly from receiving port 44a to viewing port 44b. As the sample travels to the viewing port 44b it will encounter reagent, and any analyte in the sample will begin to react with the reagent and begin to form a detectable condition, such as a color change. This detectable condition is assessed from the viewing port and can be used to determine the presence of, or to calculate the concentration of an analyte of interest. The test strip of FIG. 2 is illustrative only and many other test strip configurations may be used when practicing the present invention.

Figure 5:
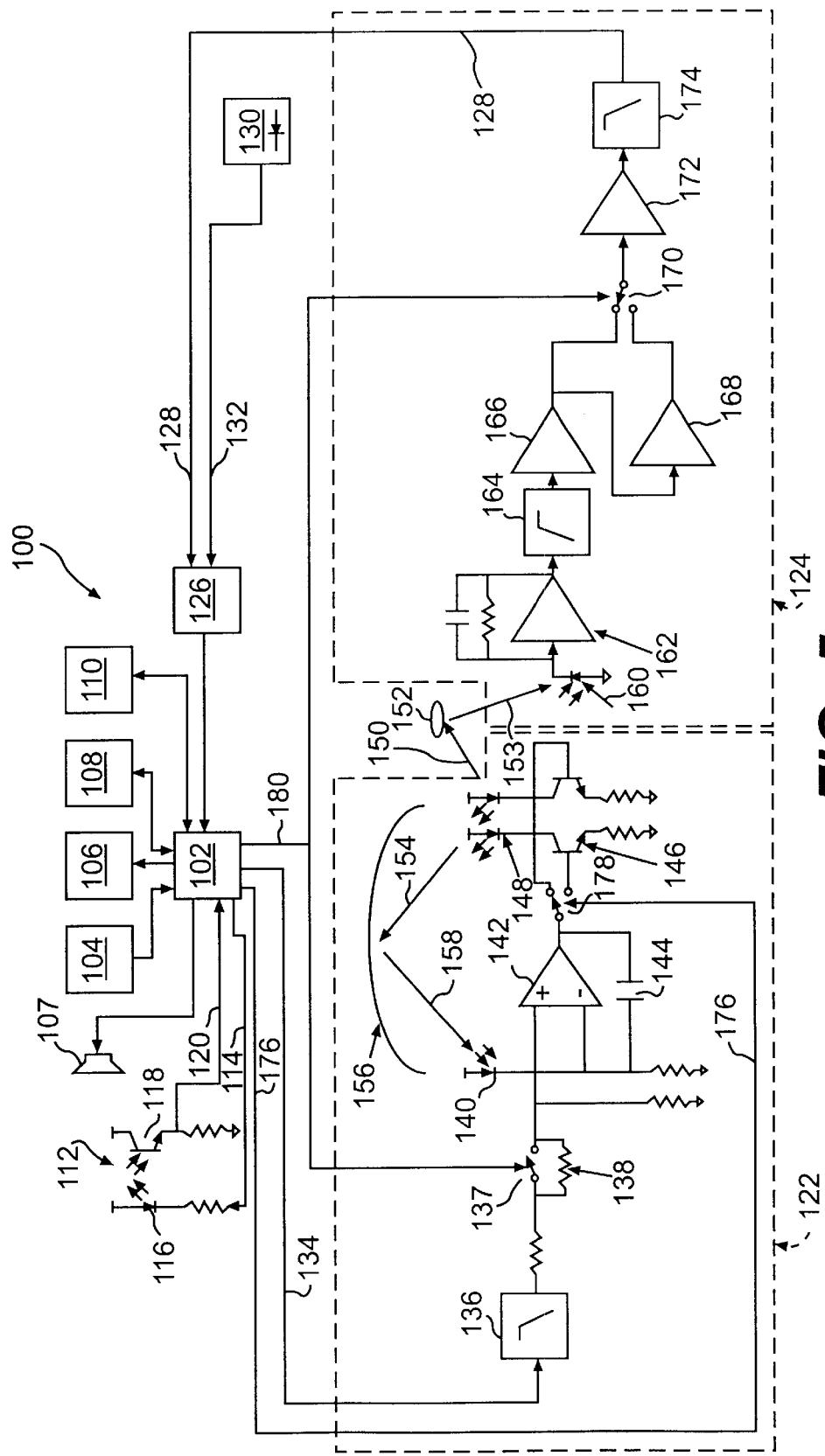
FIG. 5 is a schematic representation of a meter system according to the present invention.

Monitoring meter system 10 of the present invention includes a circuit assembly physically and electrically connected to a printed circuit board, an example of which is schematically depicted as the block diagram of FIG. 5. The circuit 100 contains a microprocessor 102 with a plurality of inputs and outputs. An exemplary embodiment of the present invention uses an 8-bit device with 60K of programmable memory. The microprocessor executes the meter instruction code. The microprocessor receives input from the user through input device 104, which can include buttons or other input devices known in the art. A display 106 and a sounder 107 or similar output devices receives data from the microprocessor for presentation to the user. A memory device 108, for example EEPROM, is also connected for input from and output to the microprocessor 102. A communication port 110 can also connected in input-output relationship with the microprocessor in known manner.

A strip sensor 112 receives a drive signal through line 114 to turn on and off photo element 116. The photo element can be an LED. Light from the photo element 116 is detected by the photodetector 118. The photodetector can be a photodiode or phototransistor. Output from the photodetector is supplied via line 120 to the microprocessor 102. The strip sensor detects when a test strip is inserted into the meter, and can be initialized by the method described in commonly assigned, copending U.S. patent application Ser. No. 09/794,037, filed concurrently herewith, the contents of which are incorporated herein by reference.

The circuit assembly can include a light intensity control circuit, represented as section 122 of the diagram, and a light detector circuit 124, discussed in further detail hereinbelow. An exemplary embodiment of the present invention operates using a DC offset ("virtual ground") of 2.5V reference (not shown) and is powered from a 1.5V AAA battery (not shown), which may include a voltage divider circuit or other power management circuitry as is known in the art.

An analog to digital (A/D) converter 126 converts analog electrical output on line 128 from the light detector circuit 124 into digital information for the microprocessor 102. In an exemplary embodiment of the invention, a 12-bit A/D converter is employed. A temperature sensor 130 provides a voltage proportional to the temperature along line 132 to the A/D converter. The microprocessor 102 can make a determination as to whether the temperature of the testing environment is within predetermined thresholds, and prohibit a user from running a test if accuracy would be negatively affected.

The light intensity control circuit (LICC) 122 will now be described. In an exemplary embodiment, the circuit is supplied by a pulse width modulated signal along line 134 from the microprocessor 102. The circuit includes a low pass filter 136, a modulator 137, a flux biasing resistor 138, a reference photodiode 140, a control loop error amplifier 142, a feedback loop compensation capacitor 144, and LED drive transistors 146. The LICC controls the drive supplied to the LEDs 148, as will be described.

The LEDs, of which there are two in the exemplary embodiment, generate light, a component 150 of which will encounter the target 152, which is the test strip or other test element inserted into the meter. Another component 154 of the light strikes a chamber reflector 156 and a portion of which 158 is reflected toward reference photodiode 140. One of the LEDs is a 660 nm LED in the exemplary embodiment, which is appropriate for detecting glucose in a test strip marketed under the tradename PRESTIGE and sold by Home Diagnostics, Inc. of Ft. Lauderdale, Fla. The exemplary embodiment can be easily modified for detecting other analytes or using other strips by changing the software and LED used to obtain a different wavelength. For instance, a 580 nm LED would be preferred for ketones using known analytical chemistry systems.

The light detector circuit (LDC) 124 will now be described. In an exemplary embodiment, the LDC includes a main photodiode 160, a transimpedance (current to voltage) amplifier 162, a high pass filter 164, an amplifier 166, and a negative gain amplifier 168. The output stage of the exemplary LDC includes a demodulator 170, a level shifting amplifier 172, and a low pass filter 174. The output stage provides a DC voltage to line 128, as set forth above. The LDC supplies an analog signal to the A/D converter, which when digitized is interpreted by the microprocessor to provide test results.

In the exemplary embodiment, input to the A/D converter is conventionally multiplexed, receiving input from lines 128 and 132, and from other signal lines not shown and not necessary to understand the present invention.

In the exemplary embodiment, two LEDs are employed, at 610 nm and 660 nm as described herein. The LEDs are selected according to the instruction code at appropriate times by the microprocessor 102 by a signal sent via line 176, which activates a switch 178. If additional LEDs are employed, then additional signal lines and switches can be added in conventional manner. The selection between the two LEDs in the exemplary embodiment is the subject of commonly assigned copending U.S. patent application Ser. No. 09/794,044, filed concurrently herewith, the contents of which are incorporated herein by reference.

The operation of the exemplary circuit 100 will now be described. A pulse width signal is produced by the microprocessor 102 along line 134. As is well known, the pulse width modulation signal is basically a 2.5V signal delivered either on or off according to a duty cycle. In a perfect square wave, the duty cycle is 50%, so that the signal is 50% on, and 50% off. Accordingly, when the signal is on, it is delivered at 2.5 volts and when it's off, it is zero volts. The signal in line 134 is averaged by the low pass filter 136 to arrive at a drive voltage for the LEDs, which will in turn determine their output. For example, for a perfect 2.5V square wave, the average voltage, and thus the output of the low pass filter 136 will be 1.25V. In this way, the power delivered to the LEDs can be modified by the microprocessor by changing the duty cycle of the pulse width modulation signal. To increase the light power, the duty cycle of the signal would be increased.

In the exemplary embodiment, the duty cycle of the pulse width modulation signal is determined during factory calibration of the meter, and the duty cycle value is permanently stored in the EEPROM. Of course, periodic calibration routines known in the art could also be employed. Further, different LEDs may have different preferred drive requirements, so different duty cycles can be utilized based on the LED in operation.

The circuit 100 employs a modulation or "chopping" function controlled by the microprocessor 102. The microprocessor 102 supplies a modulation signal via line 180 to the modulator 137 of the LICC and to the demodulator 170 of the LDC in synchrony. The chopping signal is essentially a square wave (on/off) signal supplied to drive the LEDs at a certain frequency, rather than at constant power, to eliminate noise in the signal output of the circuit. In the exemplary embodiment, a 2 kHz chop is employed. The chopping function allows the shifting of the frequency of the light signals LICC upward to a "quieter" region of the spectrum where ambient light effects can be minimized in the LDC. For example, while sunlight is 0 Hz (DC), incandescent lights have a frequency of 120 Hz. Fluorescent lights are also 120 Hz, but also have harmonic frequencies. By shifting the drive frequency of the LEDs above that of ambient light at the LICC, the LDC will be able to receive a signal at the matching frequency that is above the spectrum where most noise is encountered.

The LICC includes flux biasing resistor 138 which is in parallel with modulator 137. This resistor in parallel essentially inhibits the voltage from the low pass filter 136 from being completely turned off by the modulator 137. In this way, the chopping function, instead of modulating between full-on to full-off will modulate between full-on and low. The result is that the LEDs will be either full-on or dim, but never completely off. Several benefits are realized by this arrangement. First, because the LEDs are never dark, a positive bias is always present at the reference diode 140. As a result, when interfering ambient light reaches the reference diode 140, there is a tendency for the modulated signal to move toward ground. This positive bias helps to compensate for this tendency toward ground and allows the circuit to adapt without a change in peak-to-peak amplitude by keeping the modulated signal above ground. Second, the fact that a voltage is always present maintains control loop error amplifier 142 further above ground, which promotes better performance.

The control loop amplifier 142, in connection with the compensation capacitor 144 receives the output from the reference photodiode 140 to provide a feedback mechanism in determining the appropriate drive power for the LEDs 148.

When target 152 is illuminated by light 150 from an LED 148, reflected light 153 is received by the main photodiode 160, producing a photocurrent based on the reflectance. The photocurrent output of the photodiode 160 is supplied to transimpedance amplifier 162, which converts the photocurrent to a voltage. This voltage is conditioned by high pass filter 164, which removes noise components of the signal below the chopping frequency. It is here that the noise components of artificial lighting are filtered out, although certain harmonics of fluorescent light are eliminated after demodulation by low pass filter 174. In the exemplary embodiment, a 400 Hz cutoff frequency is employed in high pass filter 164.

The signal emerging from high pass filter 164 is basically a square wave voltage at the chopping frequency that is nominally 0.5V peak-peak maximum and centered about the vitual ground of 2.5V. To condition the output for the A/D converter, which in the exemplary embodiment operates at approximately 2.6V maximum, amplifier 166 and negative gain amplifier 168 are employed as follows. When the LED is on, the top half of the square wave is connected by level shifting amplifier 172; and when the LED is off, the bottom half of the square wave is amplified by minus unity and connected by level shifting amplifier 172. This inverts the bottom half of the square wave when the LED is off. The demodulator 170 selects between the amplifiers 166, 168 in synchrony with the modulation occurring in the LIDC at modulator 137. The resulting signal emerging from demodulator 170 is a DC signal proportional to the reflectance of the chemistry, in relation to the 2.5V reference voltage in the exemplary embodiment.

Level shifting amplifier 172, a differential amplifier, receives the DC signal from the demodulator 170, applies a gain and shifts the signal to a range acceptable to the A/D converter, which in the exemplary embodiment is approximately 2.6V maximum. Low pass filter 174 removes spiking introduced by the demodulation of the signal by amplifiers 166, 168, and also removes a large amount of the harmonics of artificial light that were shifted high by the demodulation. Further, Any DC offsets in the amplifier stages prior to the demodulations that were shifted up to the chopping frequency are also effectively filtered. The only noise left in the signal are harmonics of ambient light that are right around the chopping frequency, which in the exemplary embodiment of 2 kHz are minimal.

These remaining harmonics are of known frequency and their relationship to the chop frequency will determine their frequency. For example, the $17^{th}$ harmonic of fluorescent lighting will be 120 Hz×17=2040 Hz. If the chop frequency is 2048 HZ, which is more conveniently generated by binary digital systems than 2000 Hz, the strongest remaining interfering harmonic will be 8 Hz (|2048 Hz−2040 Hz|). Since this interfering signal is of known frequency, it can be further reduced by simple synchronous digital filtering techniques. In countries that use 50 Hz power grids, the strongest interfering frequency will be 2 Hz (the $25^{th}$ harmonic of 100 Hz=2050 Hz, |2048 Hz−2050 Hz|=2 Hz). A simple synchronous digital filtering technique that "nulls-out" both 2 Hz and 8 Hz can be implemented.

The microprocessor and code of instructions perform the calculations to arrive at the ultimate reported glucose measurement. It should be noted, however, that similar calculations can be used for deriving the amount of other analytes found in the fluid sample applied to the test strip so long as meter system 10 has been properly configured and calibrated for the particular test (analyte/reagent pair, etc.) of interest. The equations used for determining the glucose level calculations derived from Kubelka-Munk, are listed below. The first calculation is the K/S calculation and is as follows:

$$\frac{K}{S} = \frac{(1-R)^2}{2R}$$

(1) K/S Calculation

As shown by the equation, the K/S value, which compares light absorbed to light scattered, is directly related to the percentage of reflectance (R) measured by the light detector (s) as calculated by the microprocessor. The K/S calculation is then used to determine the glucose value in a linear equation. The glucose calculation is determined as follows:

$$\text{Glucose} = \frac{K}{S}m + b$$

(2) Glucose Calculation

As can be seen by the second calculation, glucose is dependent on (K/S), the slope m and intercept b.

The instruction code includes a plurality of routines for operating meter system 10. The aspects of meter software include but are not limited to: meter power-up, system diagnostics, meter readying, meter calibration, reflectance and optics calibration, code curve calibration, strip sensor calibration, temperature calibration, the blood test algorithm, test strip code management, test results storage and recall, standard strip test management, operational mode management, and user preferences setup. With the exception of the blood test algorithm detailed below, the operational aspects of the software discussed above can be in any conventional format.

The blood test algorithm discussed below is initiated immediately upon the insertion of a test strip upon which fluid containing the analyte of interest has already been placed, and a reaction already underway. The insertion of a test strip 40 into the platform 20 trips a strip sensor 112 as shown in FIG. 5 which comprises a phototransistor or photodiode that initiates the blood test algorithm. The strip insertion can be detected as described in commonly assigned copending patent application Ser. No. 09/794,037, filed concurrently herewith, the contents of which are incorporated herein by reference.

Figure 3:
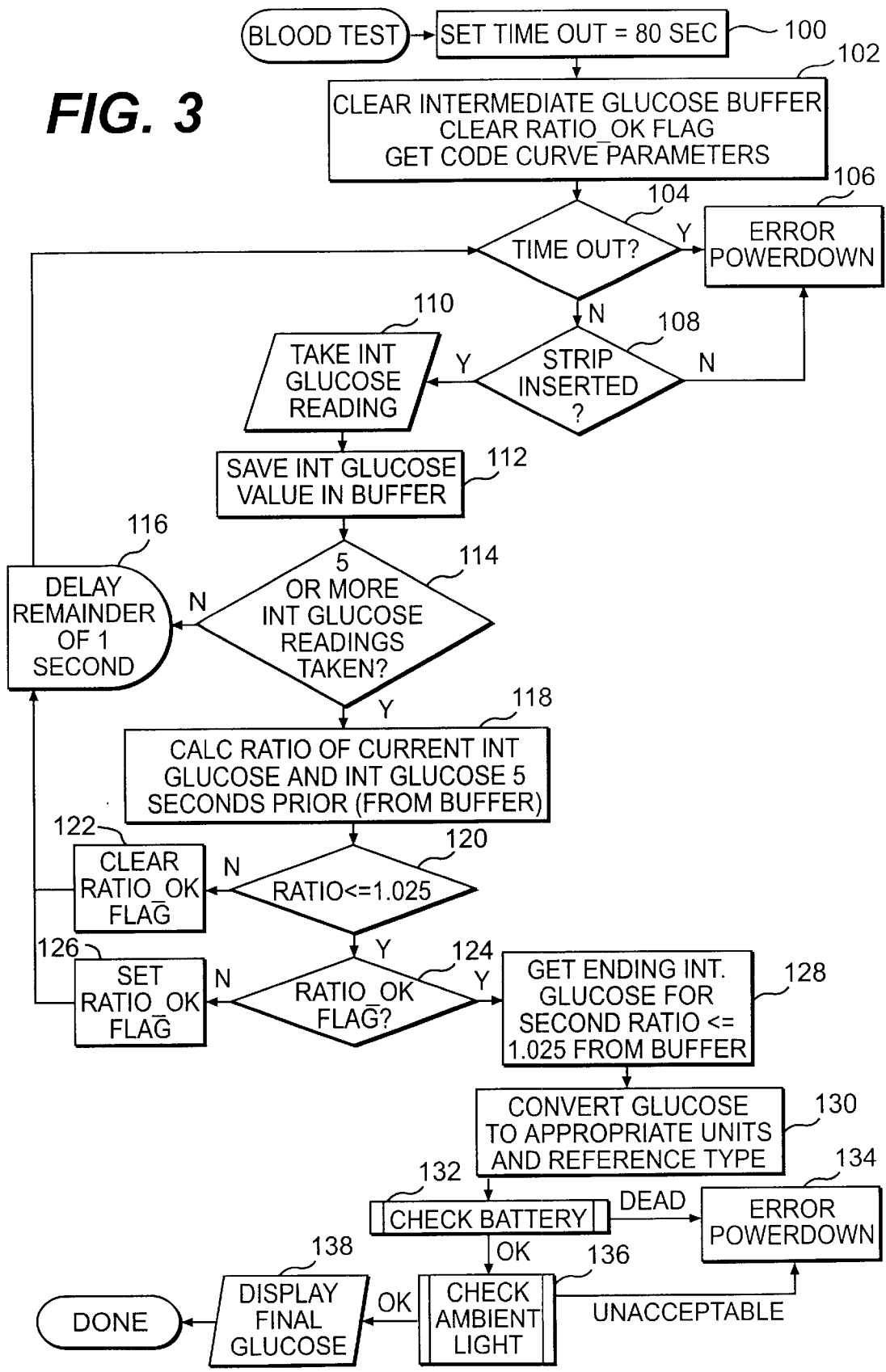
FIG. 3 illustrates a blood test subroutine of the meter system of FIG. 1.

The blood test algorithm is illustrated in FIG. 3 and includes steps 100 through 138. Once a glucose intermediate buffer and "ratio ok" flag is cleared, the code curve parameters are obtained at step 102. The code curves are calibration values stored in the memory of the device to account for slight lot-to-lot variations that occur due to strip manufacturing and processing. The subroutine then provides a check to determine whether a period of time, for example 80 seconds, have elapsed without completing the blood test procedure and arriving at a final value for glucose, or whether the strip has been removed from test strip platform, or shroud 20. If this termination period of e.g. 80 seconds has elapsed, or the test strip has been removed, an error is indicated and the meter system powers down (steps 104–108 of FIG. 3).

The next step in the blood test algorithm includes performing an intermediate glucose reading and saving the results thereof in an intermediate glucose buffer (110, 112). The subroutine then determines whether 6 or more glucose reading have occurred (114). If 6 readings have not occurred, the system waits the remainder of one second from the previous reading and checks again whether the termination period has expired, and whether the strip is still in the shroud 20 (steps 116, 104, 108). If the termination period has not elapsed and the test strip is still in place, a second reading of the test strip is performed and the glucose intermediate value is calculated and stored. This sequence continues until six or more readings are stored in the intermediate glucose buffer. These intermediate glucose values are values obtained by the glucose calculation, but may not represent the actual glucose concentration of the sample if the reaction has not stabilized. Indeed, only the last several calculated glucose values approach the actual concentration as the reaction stabilizes, as will be described below.

Once six glucose values have been obtained, a ratio of the sixth glucose value to the first glucose value is calculated at step 118. If this ratio is greater than 1.025, then another, seventh glucose value is obtained as set forth in steps 104–116 described above (120, 122). With the seventh glucose value obtained, a ratio of the seventh glucose value to the second glucose value is calculated. If again the ratio is greater than 1.025, then another, eighth glucose value is measured. This process continues with the glucose measurements taken at periodic intervals, and a ratio of the $(n)^{th}$ to the $(n-5)^{th}$ reading is calculated after each glucose value is determined, where "n" corresponds to the number of readings that have taken place. According to an embodiment of the invention, measurements can be taken at one second intervals, thus, "n" can correspond to both the number of measurements and, after the sixth measurement is taken, the number of seconds since insertion of an already reacted strip into the meter system. The successive ratio calculations are illustrated in the Glucose v. Time graph of FIG. 4. On the graph, time is depicted on the x-axis with values from glucose in mg/dl reported on the y-axis. Representative glucose values beginning 20 seconds after the insertion of an already reacting strip into the meter system are depicted. As shown at the sixth measurement on the graph, at 25 seconds, a ratio is calculated comparing the value obtained for glucose, or 258 mg/dL, to the value obtained at (25–5), or 20 seconds, which is 249 mg/dL. As depicted across the top boarder of the graph, the calculated ratio of these two glucose values is 1.036. As shown by arrow A in the figure, at 31 seconds, the ratio of the glucose value obtained at 31 seconds as compared to at (31–5), or 26 seconds, is equal to 1.019, which is less than 1.025. However, the next ratio calculated (at 27 seconds), as seen across the top border of the graph, is 1.027. Two consecutive ratios must be calculated as being less than 1.025 in order for the meter to report a final glucose value. As indicated by arrow B in the graph, once again the calculated ratio is less than 1.025, resulting from the comparison at the glucose value obtained at 34 seconds to that obtained at (34–5), or 29 seconds, resulting in a ratio of 1.023. The next calculated ratio, at arrow "C", is 1.023, satisfying the condition that two consecutive calculated ratios are less than 1.025. At this point, the final value for glucose calculated by the meter can be that obtained at arrow C, at 35 seconds, or 271 mg/dL.

When two consecutive ratios are calculated to be equal to or less than 1.025, the glucose testing end point is presumed to have been reached and the testing is deemed complete. The final calculated glucose value is then converted to the appropriate units and reference type and displayed on the LCD (steps 130, 138). The final calculated glucose value is the value calculated at time (n) of the second ratio that was calculated to be less than or equal to 1.025. A long, audible beep can be sounded and the final glucose value displayed, or further processing may occur as discussed below.

Before displaying the final glucose value, meter system 10 can check if battery voltage is sufficient, and can check if the ambient light is acceptable (steps 132, 134). If ambient light levels are not acceptable at either the reflectance or the reference detector, an error message can be displayed, and the final glucose reading is not displayed and the system is powered down (134). These tests can be performed initially or periodically and need not be performed only at the end of the test.

In an alternative embodiment of the present invention, the final glucose value displayed to the user can be obtained by averaging the second glucose values (n) from each of the ratios found to be less than or equal to the value of 1.025. Using this method for determining the final glucose value with the data of the chart of FIG. 4, the final glucose value would be the average of the glucose values at arrows "B" and "C," or (270+271)/2=270.5 mg/dL, which would in practice be rounded up or down to an integer value.

In a further alternative embodiment, the value reported to the user can be calculated from an extrapolation into the future based on the slope of line connecting the two final glucose values averaged in the previous example. In this way, the slope connecting the readings of 270 and 271 mg/dL, or 1 mg/dL/s, can be used to extrapolate glucose values into the future. Because the ratio condition of 1.025 is met two consecutive times, the reaction kinetics have practically slowed nearly to the actual theoretical end point of the reaction, and the slope of this predictive line will be relatively flat. Prediction into the future using the glucose values at arrows B and C can be employed to accurately extrapolate a final reported measurement without having to wait for reflectance measurements to be taken. In some instances, for example for particular reaction kinetics or for certain calibration code lots, it may be desirable to include a predictive element to the calculation algorithm. This prediction is also practical for tuning average statistical meter performance over time to prior art meters, allowing users of older meters to continue to utilize historical data with new data without introducing statistical error. While calculating the slope from two values is a simple method to include in extrapolating values, other known mathematical methods can be employed. For example, three or more points can be used and linear regression employed to fit a curve, or a calculation of the second derivative of the reaction curve, or a portion thereof, can also be employed. Polynomial extrapolation or curve-fitting can also be used.

Figure 4:
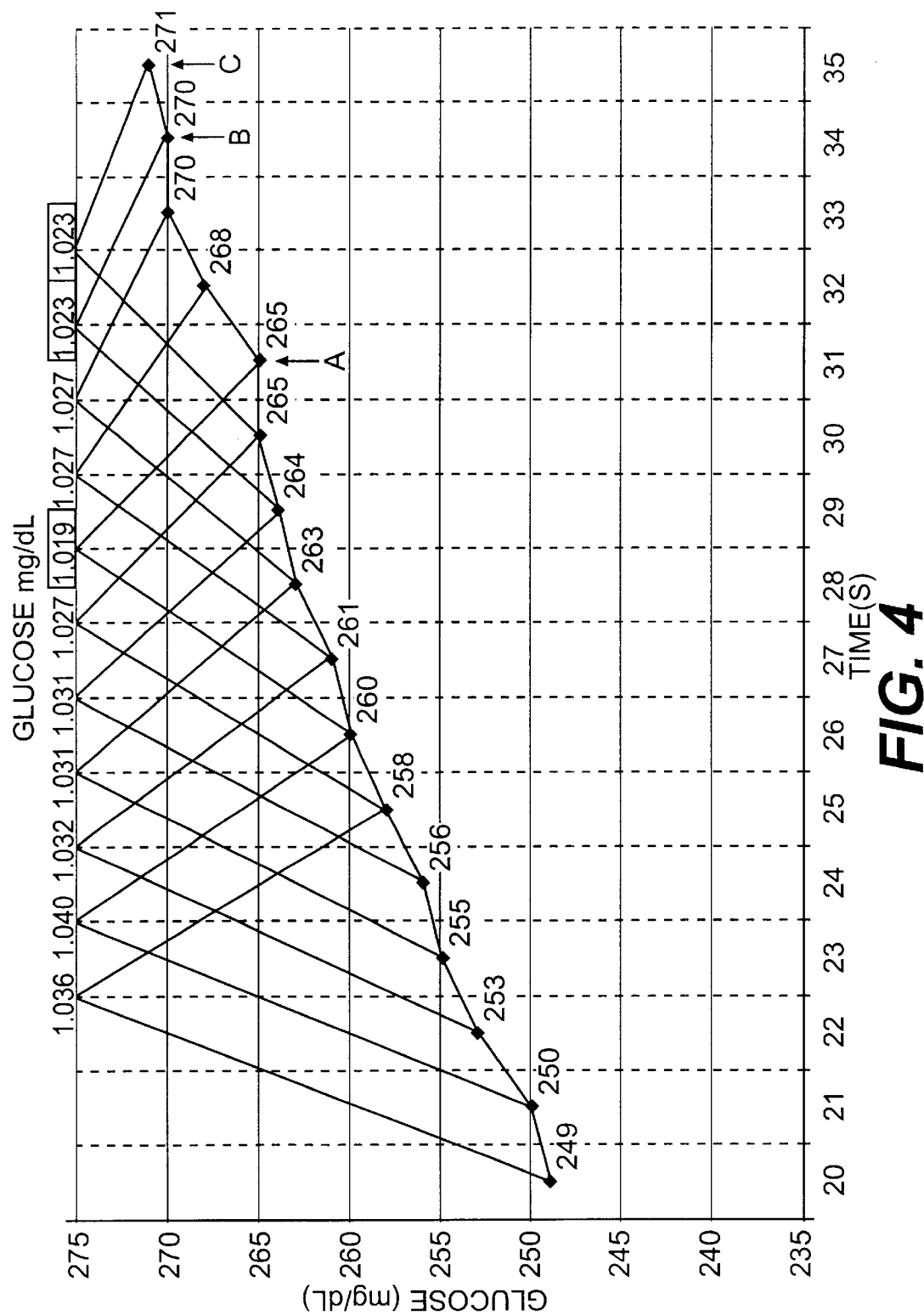
FIG. 4 illustrates a representative graph of Glucose v. Time resulting from the blood test subroutine of FIG. 3.

As shown in FIG. 4, the curve of calculated intermediate glucose values follows an upward trend, that is, has a positive slope. This should be true until the final measurements and before any extrapolation or curve fitting takes place, because the final ratio value of 1.025 is still 2.5% higher than for a perfectly flat curve, which would have a ratio value of 1.000. However, it is desirable that a negative slope is not used to predict a future glucose value. Because a persistent or significant negative slope will not normally occur during reaction measurement, the occurrence of such a negative slope could be the result of variations in meter reflectance measurements, or noise. Extrapolation using a negative slope would therefore include components of noise and undesirably impact accuracy.

A negative slope can also indicate that a fully reacted test strip has been inserted, and the decreasing glucose values calculated by the algorithm after full reaction could be the result of various phenomena, for example by the formation of late reaction products. Advantageously, managing negative slope conditions allows the meter in accordance with the present invention to exclude from testing fully reacted test strips, and avoids reporting potentially erroneous results to the user. By monitoring the ratio calculations, repetitive occurrences of ratios below 1.000, or a second derivative calculated as negative over a number of readings, the meter can signal an error condition and abort the test.

If negative slope is not persistently observed and only occurs at the very end of the testing period, a negative slope can be avoided by correcting the condition contributing to the negative slope before any extrapolation. Essentially, the meter can predict for a zero slope in these instances, in which case the extrapolated value would be equal to the final calculated glucose value. Other techniques can also be employed. For linear extrapolation, two sequential calculated glucose values used in the extrapolation can be averaged to arrive at a positive or zero slope, or the value statistically determined in a known manner to be most likely in error excluded. The second derivative of the calculated glucose values can also be employed.

Finally, monitoring meter system 10 may include a memory for storing successive final glucose values. The memory may hold a collection of successive final glucose values, such as, for example, 365 values. With the capacity of modern subminiature memory chips, a very large amount of data can be reliably stored. These final values can be recalled by pressing a control button 15. Further, meter system 10 may include a data port or a modem assembly for downloading the stored final glucose values to another computer system. The computer system receiving the downloaded final glucose values could be a home PC, or that of a doctor, or a website operator, or any other person or organization for providing assistance to the user in monitoring their glucose levels, or for collecting data on diabetes management on a community regional national or international basis. The modem assembly can be of any configuration (e.g. TCP/IP or ATM), or those having wireless communication capabilities (e.g. those using GSM, WAP, CDMA, etc.). One such modem is described in copending commonly-assigned U.S. patent application Ser. No. 09/512,919, filed Feb. 25, 2000, the contents of which are hereby incorporated by reference.

Other embodiments of the invention will be apparent to those skilled in the art from consideration of the specification and practice of the invention disclosed herein. It is intended that the specification and examples be considered as illustrative only, with a true scope and spirit of the invention being indicated by the following claims.

We claim:

1. A method for measuring an analyte in a fluid sample in a meter system, comprising:

initiating a measuring period for a fluid sample;

measuring a property of the fluid sample at each of n points in time, said points in time being spaced at predetermined intervals to form a sequence of n measurement values, where n is an integer;

comparing two nonconsecutive measurement values to determine at least one ratio;

terminating the measuring of the fluid sample when at least one of said at least one ratio meets predetermined criteria indicating a final analyte value can be accurately determined; and determining a final analyte value based on said measurement values.

2. The method for measuring an analyte in a fluid sample according to claim 1, wherein the step of measuring comprises measuring a property of an analytic test strip onto which said fluid sample has been applied.

3. The method for measuring an analyte in a fluid sample according to claim 2, wherein the analyte being measured is glucose.

4. The method for measuring an analyte in a fluid sample according to claim 2, wherein said measuring step further comprises the step of measuring a reflectance value of a test strip onto which said fluid sample has been applied.

5. The method for measuring an analyte in a fluid sample according to claim 4, wherein said predetermined intervals are each about one second in duration.

6. The method for measuring an analyte in a fluid sample according to claim 4, wherein $n \geq 6$ and said two nonconsecutive measurement values correspond to the nth measurement value and the $(n-5)^{th}$ measurement value, wherein the at least one ratio is calculated by dividing the $n^{th}$ measurement value by the $(n-5)^{th}$ measurement value.

7. The method for measuring an analyte in a fluid sample according to claim 6, wherein said at least one of said at least one ratio in said terminating step comprises two ratios calculated consecutively that meet the predetermined criteria.

8. The method for measuring an analyte in a fluid sample according to claim 7, wherein said predetermined criteria corresponds to a calculated ratio value of less than or equal to a predetermined value.

9. The method for measuring an analyte in a fluid sample according to claim 8, wherein said predetermined value is 1.025.

10. The method for measuring an analyte in a fluid sample according to claim 7, wherein the determining step includes calculating a final analyte value from a final measurement value obtained before terminating the measuring.

11. The method for measuring an analyte in a fluid sample according to claim 7, wherein the determining step includes calculating a final analyte value from an average of numerators of each of said two consecutive ratios meeting the predetermined criteria.

12. The method for measuring an analyte in a fluid sample according to claim 7, wherein the determining step further comprises the step of extrapolating the measurement values.

13. The method for measuring an analyte in a fluid sample according to claim 2, wherein said initiation step is triggered by proper insertion of the test strip in the meter system.

14. The method for measuring an analyte in a fluid sample in a meter system according to claim 1, wherein said step of determining a final analyte value further comprises extrapolating from the measurement values.

15. A meter system for measuring an analyte in a fluid sample, comprising:
   a light intensity control circuit for measuring reflectance values of an analytic test strip onto which a fluid sample has been applied; and
   a processor for
      (a) initiating a measuring period for the fluid sample;
      (b) measuring the reflectance of a portion of the test strip onto which the fluid sample has been applied at each of n points in time, said points in time being spaced at predetermined intervals to form a sequence of n calculated measurement values, where n is an integer;
      (c) comparing two nonconsecutive measurement values to determine at least one ratio,
      (d) terminating the reflectance measuring when at least one of said at least one ratio meets predetermined criteria indicating a final analyte value can be accurately determined; and
      (e) determining a final analyte value based on said measurement values; and a display for reporting said final analyte value in a user comprehensible format.

16. The meter system according to claim 15, wherein said analyte is glucose.

17. The meter system according to claim 16, wherein said predetermined intervals are each one second in duration.

18. The meter system according to claim 16, wherein $n \geq 6$ and said two nonconsecutive measurement values correspond to the $n^{th}$ measurement value and the $(n-5)^{th}$ measurement value, wherein the at least one ratio is calculated by dividing the $n^{th}$ measurement value by the $(n-5)^{th}$ measurement value.

19. The meter system according to claim 18, wherein said at least one of said at least one ratio comprises two ratios calculated consecutively that meet the predetermined criteria.

20. The meter system according to claim 19, wherein said predetermined criteria corresponds to a calculated ratio value of less than or equal to a predetermined value.

21. The meter system according to claim 20, wherein said predetermined value is 1.025.

22. The meter system according to claim 19, wherein the determining step includes calculating a final glucose value from a final reflectance value obtained before terminating the measuring.

23. The meter system according to claim 19, wherein the determining step includes calculating a final glucose value from an average of the $n^{th}$ reflectance values of each of said two consecutive ratios meeting the predetermined criteria.

24. The meter system according to claim 15, further including a strip sensor for determining whether a test strip has been properly inserted in the meter system, wherein the initiation function of the processor is triggered by the strip sensor.

25. The meter system according to claim 15, wherein said processor determines the final analyte value based on an extrapolation of the measurement values.

26. A method for measuring the concentration of glucose in a biological fluid sample in a meter system, comprising:
   initiating a measuring period for a biological fluid sample;
   measuring a property of the fluid sample at each of n points in time, said points in time being spaced at predetermined intervals to form a sequence of n measurement values, where n is an integer and greater than 2;
   comparing two nonconsecutive measurement values to determine at least one ratio;
   terminating the measuring of the biological fluid sample when at least one of said at least one ratio meets predetermined criteria indicating a final glucose concentration value can be accurately determined; and
   determining a final glucose concentration value based on said measurement values.

27. The method for measuring glucose concentration in a biological fluid sample according to claim 26, wherein the step of measuring comprises measuring an analytic test strip onto which said fluid sample has been applied.

28. The method for measuring glucose concentration in a biological fluid sample according to claim 27, wherein said measuring step further comprises the step of measuring a reflectance value of the test strip onto which said fluid sample has been applied.

29. The method for measuring glucose concentration in a biological fluid sample according to claim 28, wherein said predetermined intervals are each one second in duration.

30. The method for measuring glucose concentration in a biological fluid sample according to claim 28, wherein $n \geq 6$ and said two nonconsecutive measurement values correspond to the $n^{th}$ measurement value and the $(n-5)^{th}$ measurement value, wherein the at least one ratio is calculated by dividing the $n^{th}$ measurement value by the $(n-5)^{th}$ measurement value.

31. The method for measuring glucose concentration in a biological fluid sample according to claim 30, wherein said at least one of said at least one ratio in said terminating step comprises two ratios calculated consecutively that meet the predetermined criteria.

32. The method for measuring glucose concentration in a biological fluid sample according to claim 31, wherein said predetermined criteria corresponds to a calculated ratio value of less than or equal to a predetermined value.

33. The method for measuring glucose concentration in a biological fluid sample according to claim 32, wherein said predetermined value is 1.025.

34. The method for measuring glucose concentration in a biological fluid sample according to claim 31, wherein the determining step includes calculating a final glucose value from a final measurement value obtained before terminating the measuring.

35. The method for measuring glucose concentration in a biological fluid sample according to claim 31, wherein the determining step includes calculating a final glucose value from an average of the $n^{th}$ measurement values of each of said two consecutive ratios meeting the predetermined criteria.

36. The method for measuring glucose concentration in a biological fluid sample according to claim 27, wherein said initiation step is triggered by proper insertion of the test strip in the meter system.

* * * * *